(12) United States Patent
Godo

(10) Patent No.: US 10,881,281 B2
(45) Date of Patent: Jan. 5, 2021

(54) CAPSULE ENDOSCOPE HAVING AN IMAGE SENSOR AND A SENSOR FOR DETECTING A PHYSICAL QUANTITY AND CAPSULE ENDOSCOPE SYSTEM INCLUDING THE CAPSULE ENDOSCOPE

(71) Applicant: OLYMPUS CORPORATION, Tokyo (JP)

(72) Inventor: Hirokazu Godo, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 413 days.

(21) Appl. No.: 15/995,728

(22) Filed: Jun. 1, 2018

(65) Prior Publication Data

US 2018/0279863 A1 Oct. 4, 2018

Related U.S. Application Data

(63) Continuation of application No. PCT/JP2015/084662, filed on Dec. 10, 2015.

(51) Int. Cl.
*A61B 1/00* (2006.01)
*A61B 1/045* (2006.01)
(Continued)

(52) U.S. Cl.
CPC .......... *A61B 1/041* (2013.01); *A61B 1/00009* (2013.01); *A61B 1/045* (2013.01);
(Continued)

(58) Field of Classification Search
CPC . A61B 1/041; A61B 1/00009; A61B 1/00006; A61B 1/045; A61B 1/00036;
(Continued)

(56) References Cited

U.S. PATENT DOCUMENTS

| | | | |
|---|---|---|---|
| 6,709,387 B1 | 3/2004 | Glukhovsky et al. | |
| 2004/0073087 A1* | 4/2004 | Glukhovsky | A61B 1/00158 600/109 |
| 2006/0184039 A1* | 8/2006 | Avni | A61B 5/0031 600/476 |
| 2008/0242931 A1 | 10/2008 | Nishino | |
| 2009/0099418 A1* | 4/2009 | Kimoto | A61B 1/00036 600/118 |
| 2009/0192348 A1 | 7/2009 | Nishino | |

(Continued)

FOREIGN PATENT DOCUMENTS

| | | |
|---|---|---|
| JP | 2008-237639 A | 10/2008 |
| JP | 2009-172287 A | 8/2009 |

(Continued)

OTHER PUBLICATIONS

Notice of Allowance dated Aug. 6, 2019 in Japanese Patent Application No. 2017-554737.

(Continued)

*Primary Examiner* — John P Leubecker
(74) *Attorney, Agent, or Firm* — Scully, Scott, Murphy & Presser, P.C.

(57) ABSTRACT

A capsule endoscope includes a sensor, an analyzer, a counter, a signal generator, and an imager. A count value becomes a reference value when an imaging synchronization signal is generated. When the count value changes from the reference value to a first predetermined value, the signal generator generates the imaging synchronization signal. A second time that is necessary for the count value to change from the reference value to the first predetermined value is fixed or variable. The second time is longer than a first time in a case in which the second times is fixed. A maximum value of the second time is longer than the first time in a case in which the second time is variable.

15 Claims, 15 Drawing Sheets

(51) Int. Cl.
*A61B 1/04* (2006.01)
*A61B 5/00* (2006.01)
*A61B 5/103* (2006.01)
*A61B 5/07* (2006.01)
*A61B 17/00* (2006.01)
*A61B 34/20* (2016.01)

(52) U.S. Cl.
CPC .............. *A61B 5/073* (2013.01); *A61B 5/103* (2013.01); *A61B 5/6861* (2013.01); *A61B 5/7285* (2013.01); *A61B 2017/00075* (2013.01); *A61B 2034/2048* (2016.02); *A61B 2562/0219* (2013.01)

(58) Field of Classification Search
CPC .......... A61B 5/073; A61B 2017/00075; A61B 2562/0219
See application file for complete search history.

(56) References Cited

U.S. PATENT DOCUMENTS

2014/0003418 A1* 1/2014 Khait ................ A61B 1/00016
370/350
2017/0020374 A1* 1/2017 Duan ................ A61B 1/00036

FOREIGN PATENT DOCUMENTS

| JP | 2010-524557 A | 7/2010 |
| JP | 2012-071186 A | 4/2012 |
| JP | 2015-070915 A | 4/2015 |
| WO | 2009/031711 A1 | 3/2009 |

OTHER PUBLICATIONS

International Search Report dated Mar. 15, 2016 issued in PCT/JP2015/084662.

* cited by examiner

CAPSULE ENDOSCOPE HAVING AN IMAGE SENSOR AND A SENSOR FOR DETECTING A PHYSICAL QUANTITY AND CAPSULE ENDOSCOPE SYSTEM INCLUDING THE CAPSULE ENDOSCOPE

This application is a continuation application based on PCT Application No. PCT/JP 2015/084662 filed on Dec. 10, 2015, the content of which is incorporated herein by reference.

BACKGROUND OF THE INVENTION

Field of the Invention

The present invention relates to a capsule endoscope and capsule endoscope system.

Description of Related Art

When a capsule endoscope passes through the inside of an organ of an examinee, the capsule endoscope moves relative to the human body. In a case in which the moving speed is high, it is preferable to increase the frame rate of imaging to mitigate image omission in a test subject. In addition, when the capsule endoscope has stopped relative to the human body, it is preferable for the frame rate of imaging in the capsule endoscope to be decreased to reduce power consumption.

A system disclosed in U.S. Pat. No. 6,709,387 determines a frame rate of imaging on the basis of an output of a sensor detecting the motion of a capsule. This system can determine the frame rate of imaging on the basis of a result of comparison between two images output from the capsule. A device external to the capsule determines the frame rate and instructs the capsule on the determined frame rate.

SUMMARY OF THE INVENTION

According to a first aspect of the present invention, a capsule endoscope includes a sensor, an analyzer, a counter, a signal generator, and an imager. The sensor detects a physical quantity. The analyzer analyzes the physical quantity and periodically generates first data based on the physical quantity at intervals of a first time. A count value of the counter increases or decreases from a reference value. The signal generator generates an imaging synchronization signal on the basis of the first data and generates the imaging synchronization signal on the basis of a result of comparison between the count value and a first predetermined value. The imager performs imaging on the basis of the imaging synchronization signal. The count value becomes the reference value when the imaging synchronization signal is generated. The signal generator generates the imaging synchronization signal when the count value becomes the first predetermined value or more in accordance with an increase of the count value from the reference value or when the count value becomes the first predetermined value or less in accordance with a decrease of the count value from the reference value. A second time that is necessary for the count value to change from the reference value to the first predetermined value is fixed or variable. The second time is longer than the first time in a case in which the second times is fixed. The maximum value of the second time is longer than the first time in a case in which the second time is variable.

According to a second aspect of the present invention, in the first aspect, the reference values may include a first reference value and a second reference value. The second reference value is either the same as the first reference value or different from the first reference value. The count value may become a second reference value smaller than the first predetermined value when the first reference value is less than the first predetermined value and when the count value becomes the first predetermined value or more in accordance with an increase of the count value from the first reference value. The count value may become a second reference value larger than the first predetermined value when the first reference value is more than the first predetermined value and when the count value becomes the first predetermined value or less in accordance with a decrease of the count value from the first reference value.

According to a third aspect of the present invention, in the first aspect, the count value may increase in synchronization with generation of the first data by the analyzer.

According to a fourth aspect of the present invention, in the first aspect, the count value may decrease in synchronization with generation of the first data by the analyzer.

According to a fifth aspect of the present invention, in the third aspect, a second predetermined value may be added to the count value in synchronization with the generation of the first data by the analyzer. The second predetermined value is either the same as the first predetermined value or different from the first predetermined value.

According to a sixth aspect of the present invention, in the fourth aspect, a second predetermined value may be subtracted from the count value in synchronization with the generation of the first data by the analyzer. The second predetermined value is either the same as the first predetermined value or different from the first predetermined value.

According to a seventh aspect of the present invention, in the third aspect, a value corresponding to the first data may be added to the count value in synchronization with the generation of the first data by the analyzer.

According to an eighth aspect of the present invention, in the fourth aspect, a value corresponding to the first data may be subtracted from the count value in synchronization with the generation of the first data by the analyzer.

According to a ninth aspect of the present invention, in the third aspect, a value acquired by adding a second predetermined value and a value corresponding to the first data may be added to the count value in synchronization with the generation of the first data by the analyzer. The second predetermined value is either the same as the first predetermined value or different from the first predetermined value.

According to a tenth aspect of the present invention, in the fourth aspect, a value acquired by adding the second predetermined value and the value corresponding to the first data may be subtracted from the count value in synchronization with the generation of the first data by the analyzer. The second predetermined value is either the same as the first predetermined value or different from the first predetermined value.

According to a eleventh aspect of the present invention, in the first aspect, the reference value may be a third predetermined value different from the first predetermined value.

According to an twelfth aspect of the present invention, in the first aspect, the count value may become the reference value by subtracting a fourth predetermined value from the count value when the reference value is less than the first predetermined value and when the count value becomes the first predetermined value or more in accordance with an increase of the count value from the reference value. The count value may become the reference value acquired by adding the fourth predetermined value to the count value when the reference value is more than the first predetermined value and when the count value becomes the first predetermined value or less in accordance with a decrease of the count value from the reference value. The fourth predetermined value may be either the same as the first predetermined value or different from the first predetermined value.

According to a thirteenth aspect of the present invention, in the first aspect, the analyzer may periodically generate the first data at intervals of the first time on the basis of second data based on the physical quantity and on the basis of third data that is independent from the second data.

According to a fourteenth aspect of the present invention, in any one of the first to ninth aspects, the sensor may periodically detect a movement of the capsule endoscope at intervals of a third time. The third time is the first time or less. The analyzer may analyze the movement and periodically generate the first data based on the movement at intervals of the first time.

According to a fifteenth aspect of the present invention, a capsule endoscope system includes a capsule endoscope and a radio communication device. The capsule endoscope includes a sensor, a first communicator, a counter, a signal generator, and an imager. The sensor detects a physical quantity. The first communicator wirelessly transmits sensor data representing the physical quantity to the radio communication device and wirelessly receives first data from the radio communication device periodically at intervals of a first time. A count value of the counter increases or decreases from a reference value. The signal generator generates an imaging synchronization signal on the basis of the first data and generates the imaging synchronization signal on the basis of a result of comparison between the count value and a first predetermined value. The imager performs imaging on the basis of the imaging synchronization signal. The radio communication device includes a second communicator and an analyzer. The second communicator wirelessly receives the sensor data from the capsule endoscope and wirelessly transmits the first data to the capsule endoscope periodically at intervals of the first time. The analyzer analyzes the physical quantity on the basis of the sensor data and periodically generates the first data based on the physical quantity at intervals of the first time. The count value becomes the reference value when the imaging synchronization signal is generated. The signal generator generates the imaging synchronization signal when the count value becomes the first predetermined value or more in accordance with an increase of the count value from the reference value or when the count value becomes the first predetermined value or less in accordance with a decrease of the count value from the reference value. A second time that is necessary for the count value to change from the reference value to the first predetermined value is fixed or variable. The second time is longer than the first time in a case in which the second times is fixed. The maximum value of the second time is longer than the first time in a case in which the second time is variable.

DETAILED DESCRIPTION OF THE INVENTION

A reference aspect and embodiments of the present invention will be described below with reference to the drawings.
(Reference Aspect)

Figure 15:
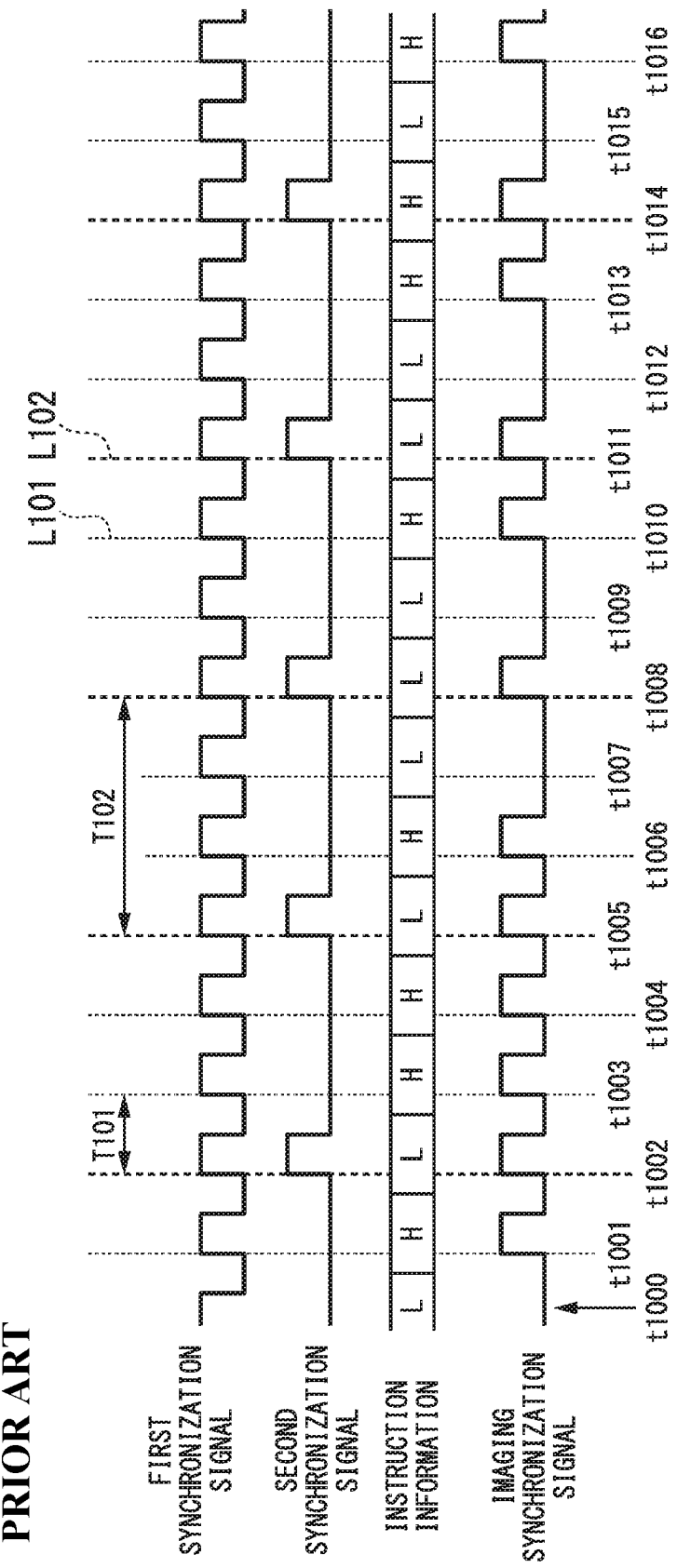
FIG. 15 is a timing diagram showing the operation of a capsule endoscope according to a reference aspect of the present invention.

FIG. 15 is a timing diagram showing the operation of a capsule endoscope according to a reference aspect of the present invention. In FIG. 15, waveforms of a first synchronization signal, a second synchronization signal, and an imaging synchronization signal and instruction information are shown. For the first synchronization signal, the second synchronization signal, and the imaging synchronization signal, the vertical direction represents the voltage in FIG. 15. In FIG. 15, time advances toward the right side.

The first synchronization signal and the second synchronization signal have constant cycles. The first synchronization signal periodically changes at intervals of a first time T101. In other words, the cycle of the first synchronization signal is the same as the first time T101. The second synchronization signal periodically changes at intervals of a second time T102. In other words, the cycle of the second synchronization signal is the same as the second time T102. The cycle of the second synchronization signal is longer than the cycle of the first synchronization signal. In other words, the first synchronization signal is a synchronization signal for imaging at a high frame rate, and the second synchronization signal is a synchronization signal for imaging at a low frame rate. Thin lines L101 represent reference timings of the first synchronization signal. Thick lines L102 represent reference timings of the first synchronization signal and the second synchronization signal. In FIG. 15, the reference timings coincide with rising edges of each signal. An interval between lines L101 and L101 or an interval between lines L101 and L102 is the first time T101. An interval between lines L102 and L102 is the second time T102.

The instruction information instructs the frame rate of imaging. The instruction information is "H" or "L." Here, "H" represents an instruction for increasing the frame rate. In a case in which the movement of the capsule endoscope is great, the instruction information is "H." "L" represents an instruction for decreasing the frame rate. In a case in which the movement of the capsule endoscope is small, the instruction information is "L." The instruction information is generated on the basis of an output of a sensor or the like. In the example shown in FIG. 15, the instruction information is updated at intervals of the first time T101. There may be cases in which updated instruction information is the same as instruction information before the update.

The imaging synchronization signal has a high level and a low level. When the imaging synchronization signal is at a high level, an imaging synchronization signal is valid. On the other hand, when the imaging synchronization signal is at a low level, an imaging synchronization signal is invalid. When the imaging synchronization signal is valid, imaging is performed. On the basis of the instruction information, one of the first synchronization signal and the second synchronization signal is selected, and the selected signal is output as an imaging synchronization signal. In a case in which the instruction information is "H," the first synchronization signal is output as an imaging synchronization signal. On the other hand, in a case in which the instruction information is "L," the second synchronization signal is output as an imaging synchronization signal.

At a timing t1000, the instruction information is "L." For this reason, the second synchronization signal is output as an imaging synchronization signal at the timing t1000. At the timing t1000, the second synchronization signal is at the low level. As a result, the imaging synchronization signal is invalid at the timing t1000.

At a timing t1001, the instruction information is "H." For this reason, the first synchronization signal is output as an imaging synchronization signal at the timing t1001. At the timing t1001, the first synchronization signal is at the high level. As a result, the imaging synchronization signal is valid at the timing t1001.

At a timing t1002, the instruction information is "L." For this reason, the second synchronization signal is output as an imaging synchronization signal at the timing t1002. At the timing t1002, the second synchronization signal is at the high level. As a result, the imaging synchronization signal is valid at the timing t1002.

At timings t1003 and t1004, the instruction information is "H," and the first synchronization signal is at the high level. For this reason, similar to the timing t1001, the imaging synchronization signal is valid at the timings t1003 and t1004.

At a timing t1005, the instruction information is "L," and the second synchronization signal is at the high level. For this reason, similar to the timing t1002, the imaging synchronization signal is valid at the timing t1005.

At a timing t1006, the instruction information is "H," and the first synchronization signal is at the high level. For this reason, similar to the timing t1001, the imaging synchronization signal is valid at the timing t1006.

At a timing t1007, the instruction information is "L," and the second synchronization signal is at the low level. For this reason, similar to the timing t1000, the imaging synchronization signal is invalid at the timing t1007.

At a timing t1008, the instruction information is "L," and the second synchronization signal is at the high level. For this reason, similar to the timing t1002, the imaging synchronization signal is valid at the timing t1005.

A detailed description of operations in a period from a timing t1009 to a timing t1016 will not be presented here. At timings t1010, t1011, t1013, t1014, and t1016, the imaging synchronization signal is valid. At timings t1009, t1012, and t1015, the imaging synchronization signal is invalid.

A period from the timing t1001 at which a valid imaging synchronization signal is output to the timing t1002 at which a valid imaging synchronization signal is output again is the first time T101. At the timing t1002, although the instruction information is "L," an imaging interval is short. Similarly, at the timings t1005, t1008, and t1011, the instruction information is "L," and a valid imaging synchronization signal is output. Also at these timings, although the instruction information is "L," an imaging interval is short. Since the imaging interval is short, there is a possibility that unnecessary imaging may be performed. In the operation shown in FIG. 15, in a case in which the instruction information frequently switches between "H" and "L," when the instruction information is "L," a valid imaging synchronization signal may be more easily output. In other words, unnecessary imaging may easily be performed. By performing unnecessary imaging, the power consumption of the capsule endoscope increases.

First Embodiment

Figure 1:
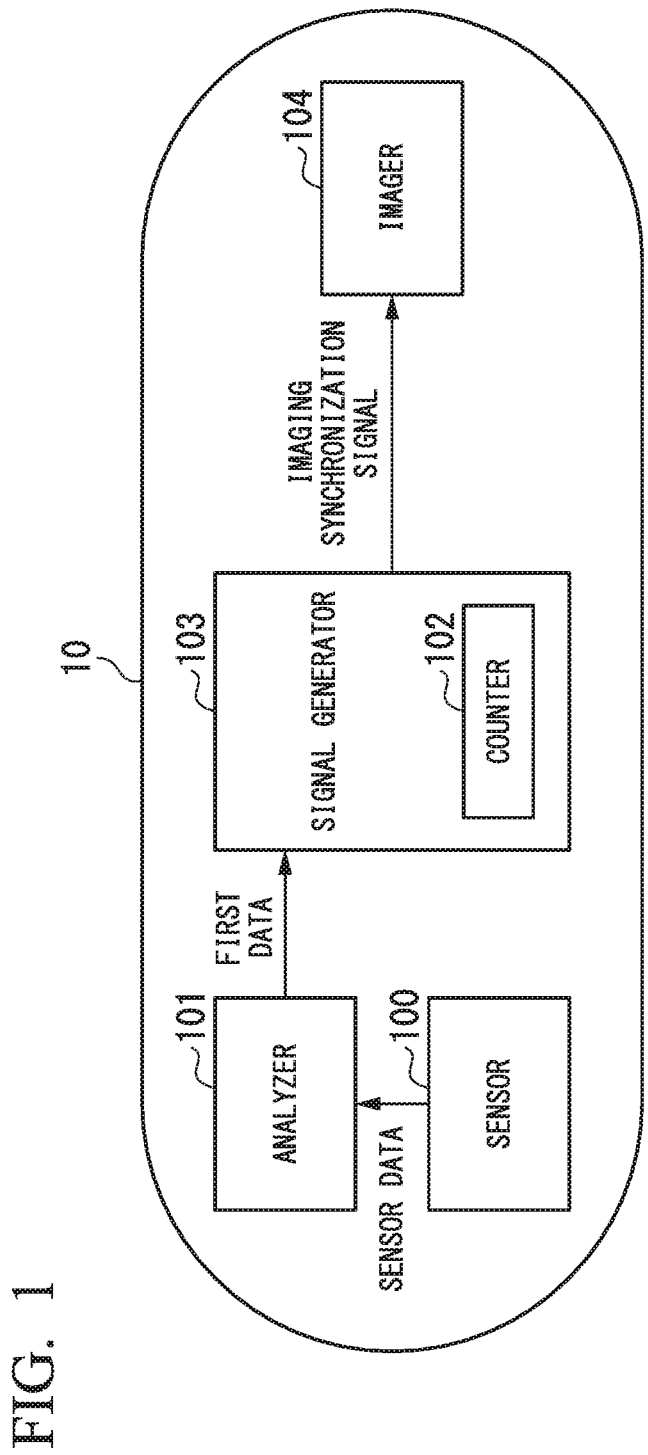
FIG. 1 is a block diagram showing the configuration of a capsule endoscope according to a first embodiment of the present invention.

FIG. 1 shows the configuration of a capsule endoscope 10 according to a first embodiment of the present invention. As shown in FIG. 1, the capsule endoscope 10 includes a sensor 100, an analyzer 101, a counter 102, a signal generator 103, and an imager 104. Each component shown in FIG. 1 is hardware.

The sensor 100 detects a physical quantity. The analyzer 101 analyzes the physical quantity detected by the sensor 100 and periodically generates first data based on the physical quantity at intervals of a first time. A count value of the counter 102 increases or decreases from a reference value. The signal generator 103 generates an imaging synchronization signal on the basis of first data and generates an imaging synchronization signal on the basis of a result of comparison between the count value and a first predetermined value. The imager 104 performs imaging on the basis of the imaging synchronization signal. When the imaging synchronization signal is generated, the count value becomes the reference value. When the count value is the first predetermined value or more in accordance with an increase of the count value from the reference value, or when the count value is the first predetermined value or less in accordance with a decrease of the count value from the reference value, the signal generator 103 generates an imaging synchronization signal. A second time that is necessary for the count value to change from the reference value to the first predetermined value is fixed or variable. In a case in which the second time is fixed, the second time is longer than the first time. On the other hand, in a case in which the second time is variable, the maximum value of the second time is longer than the first time.

Details of each component shown in FIG. 1 will be described. The sensor 100 periodically detects a physical quantity at intervals of the first time and generates sensor data representing the detected physical quantity. A cycle at which the sensor 100 generates sensor data is the same as the first time. For example, the sensor 100 may be a movement sensor. The sensor 100 may periodically detect the movement of the capsule endoscope 10 at intervals of the first time and generate sensor data representing the detected movement of the capsule endoscope 10. For example, the sensor 100 may be at least one of an acceleration sensor, a speed sensor, a magnetic sensor, and an angular velocity sensor. Accordingly, the sensor 100 can acquire data of at least one of an acceleration, a speed, an angular velocity, and magnetism. The sensor 100 outputs sensor data to the analyzer 101.

In a case in which the sensor 100 is an acceleration sensor, the sensor data is acceleration data. The acceleration data is measurement results of the acceleration of the capsule endoscope 10.

In a case in which the sensor 100 is a speed sensor, the sensor data is speed data. The speed data is a result of measurement of the speed of the capsule endoscope 10.

By integrating a speed represented by the speed data, position data may be acquired. From amounts of change of position data at a plurality of times, the movement of the capsule endoscope 10 can be detected.

In a case in which the sensor 100 is a magnetic sensor, the sensor data is magnetic data. The magnetic data is a result of measurement of terrestrial magnetism. By using a magnetic sensor that can perform measurement in directions in three dimensions, the posture of the capsule endoscope 10 can be detected. Thus, from the amount of change of magnetic data at a plurality of times, the movement of the capsule endoscope 10 can be detected.

In a case in which the sensor 100 is an angular velocity sensor, the sensor data is angular velocity data. The angular velocity data is a result of measurement of an angular velocity of the capsule endoscope 10.

The analyzer 101 is configured as one or a plurality of processors. Each of the processors includes a central processing unit (CPU) a digital signal processor (DSP), an application specific integrated circuit (ASIC), a field-programmable gate array (FPGA), or the like. The analyzer 101 analyzes sensor data and generates first data representing a result of the analysis. The analyzer 101 outputs the first data to the signal generator 103.

For example, the analyzer 101 compares sensor data with a predetermined threshold or compares the amount of change of sensor data at a plurality of times with a predetermined threshold. In a case in which the sensor data is acceleration data, the analyzer 101 may calculate speed data or position data on the basis of the acceleration data. The first data is a result of the comparison described above.

The sensor 100 may periodically detect the movement of the capsule endoscope 10 at intervals of a third time. The third time is the first time or less. The analyzer 101 may analyze a movement detected by the sensor 100 and periodically generate first data based on the movement at intervals of the first time.

The counter 102 counts the first data or a cycle signal. For example, the cycle signal is generated by the signal generator 103. The counter 102 is configured as one or a plurality of counter circuits. The counter 102 can perform at least one of counting up and counting down. A count value of the counter 102 is set to a reference value when counting is started. The count value increases or decreases from the reference value in accordance with the counting. When an imaging synchronization signal is generated, the count value is set to the reference value again. The reference value is not limited to a constant value. The counting using the counter 102 is performed at intervals of the first time. In other words, the count value increases or decreases in synchronization with the generation of the first data by the analyzer 101. For example, a second time that is necessary for the count value to change from the reference value to a first predetermined value is n times the first time. Here, n is an integer of two or more. The operation of the counter 102 does not necessarily be synchronized with the generation of the first data by the analyzer 101.

Reference values may include a first reference value and a second reference value. The second reference value is either the same as the first reference value or different from the first reference value. When the first reference value is less than the first predetermined value and the count value becomes the first predetermined value or more in accordance with an increase of the count value from the first reference value, the count value becomes the second reference value that is less than the first predetermined value. When the first reference value is more than the first predetermined value and the count value becomes the first predetermined value or less in accordance with a decrease of the count value from the first reference value, the count value becomes the second reference value that is more than the first predetermined value.

The signal generator 103 (signal generating circuit) is a digital signal processing circuit. The signal generator 103 may be configured as one or a plurality of processors. The analyzer 101 and the signal generator 103 may be configured as one piece of hardware. The counter 102 is disposed inside the signal generator 103. The counter 102 may be independent from the signal generator 103. The signal generator 103 generates an imaging synchronization signal on the basis of the first data and generates an imaging synchronization signal on the basis of the count value of the counter 102. In a case in which the first data satisfies a predetermined condition, the signal generator 103 generates an imaging synchronization signal. When the count value becomes the first predetermined value or more in accordance with an increase of the count value from the reference value, the signal generator 103 generates an imaging synchronization signal. Alternatively, when the count value becomes the first predetermined value or less in accordance with a decrease of the count value from the reference value, the signal generator 103 may generate an imaging synchronization signal. There are cases in which the count value of the counter 102 changes on the basis of the first data, and the signal generator 103 generates an imaging synchronization signal on the basis of the count value. In such cases, the first data is reflected in the timing of the imaging synchronization signal.

The imager 104 is an imaging device (image sensor). The imager 104 acquires an image (image data) by performing imaging at an imaging timing based on the imaging synchronization signal. A test object imaged by the imager 104 is an organ inside a human body. The image acquired by the imager 104 may be wirelessly transmitted to a receiving device disposed outside the body.

For example, the functions of the analyzer 101 and the signal generator 103 can be realized as functions of software when a program including commands defining the operations of the analyzer 101 and the signal generator 103 is read and executed by a computer of the capsule endoscope 10. This program, for example, may be provided using a "computer-readable recording medium" such as a flash memory. In addition, the program described above may be transmitted to the capsule endoscope 10 from a computer including a storage device in which the program is stored or the like through a transmission medium or using a transmission wave inside a transmission medium. The "transmission medium" transmitting the program is a medium having a function of transmitting information such as a network (communication network) such as the Internet or a communication circuit line (communication line) such as a telephone line. In addition, the program described above may realize a part of the functions described above. Furthermore, the program described above may be a differential file (differential program) that can realize the functions described above by being combined with a program that has already been recorded in the computer.

(First Operation)

Figure 2:
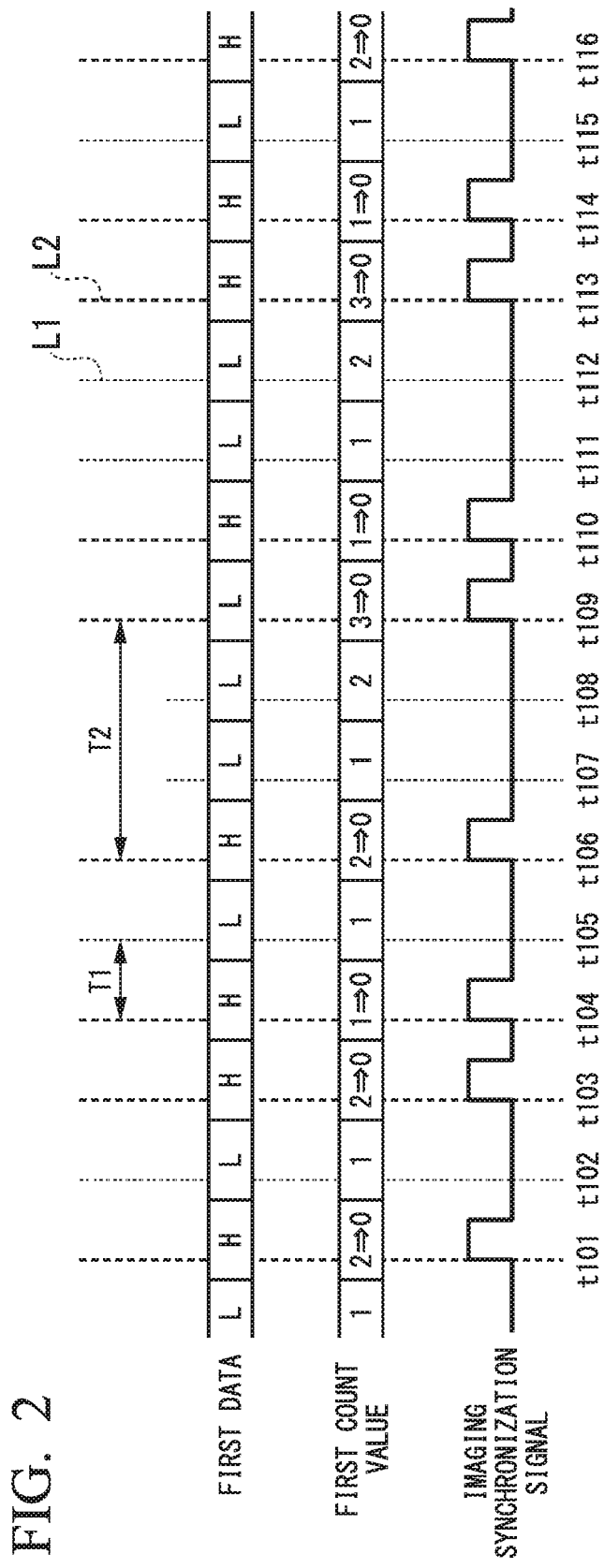
FIG. 2 is a timing diagram showing a first operation of the capsule endoscope according to the first embodiment of the present invention.

FIG. 2 shows a first operation of the capsule endoscope 10. In FIG. 2, waveforms of first data, a first count value, and an imaging synchronization signal are shown. For the imaging synchronization signal, the vertical direction represents the voltage in FIG. 2. In FIG. 2, time advances toward the right side.

The first data is "H" or "L." "H" represents that the movement of the capsule endoscope 10 is great. "L" represents that the movement of the capsule endoscope 10 is small. The first data is updated at intervals of a first time T1. There are cases in which updated first data is the same as the first data before update.

The first count value increases from a reference value. When the first count value becomes a first predetermined value or more, the signal generator 103 generates an imaging synchronization signal. The first count value increases in synchronization with the generation of the first data by the analyzer 101. A second predetermined value is added to the first count value in synchronization with the generation of the first data by the analyzer 101. The second predetermined value is either the same as the first predetermined value or different from the first predetermined value. The reference value is a third predetermined value different from the first predetermined value.

The counter 102 generates a first count value by counting the cycle signal. The cycle of the cycle signal counted by the counter 102 is the same as the first time T1. The counter 102 generates a first count value every first time T1. The first count value increases by a second predetermined value every first time T1. When the first count value becomes a first predetermined value or more, the first count value changes to a reference value. The reference value is "0." The first predetermined value is "3." The second predetermined value is "1." The second time that is necessary for the first count value to change from the reference value to the first predetermined value is fixed.

A cycle at which the signal generator 103 refers to the first data and the first count value is fixed. The signal generator 103 refers to the first data and the first count value at intervals of the first time T1. Thin lines L1 and thick lines L2 represent timings at which there is a possibility of the imaging synchronization signals being generated. The lines L1 and L2 coincide with rising edges of the imaging synchronization signal at timings at which imaging synchronization signals are generated. The signal generator 103 generates an imaging synchronization signal based on the first data at the timing of the line L1 or the line L2. The signal generator 103 generates an imaging synchronization signal based on the first count value at the timing of the line L2. An interval between the line L1 and the line L1 or an interval between the line L1 and the line L2 is the first time T1. In a case in which the first data is "H" or in a case in which the first count value is a first predetermined value or more, the signal generator 103 generates an imaging synchronization signal.

The imaging synchronization signal has a high level and a low level. When the imaging synchronization signal is at the high level, the imaging synchronization signal is valid. On the other hand, when the imaging synchronization signal is at the low level, the imaging synchronization signal is invalid. When the imaging synchronization signal is valid, the imager 104 performs imaging. The imaging synchronization signal may be valid when the imaging synchronization signal is at the low level, and the imaging synchronization signal may be invalid when the imaging synchronization signal is at the high level.

At a timing t101, the first data is "H." At the timing t101, "1" that is the second predetermined value is added to the first count value, whereby the first count value changes to "2." Since the first data is "H," at the timing t101, the signal generator 103 generates a valid imaging synchronization signal. At the timing t101, the first count value changes to "0" that is the reference value.

At a timing t102, the first data is "L." At the timing t102, "1" that is the second predetermined value is added to the first count value, whereby the first count value changes to "1." At this time, the first count value is less than "3" that is the first predetermined value. For this reason, at the timing t102, the imaging synchronization signal is invalid.

At a timing t103, the first data is "H." At the timing t103, "1" that is the second predetermined value is added to the first count value, whereby the first count value changes to "2." Since the first data is "H," at the timing t103, the signal generator 103 generates a valid imaging synchronization signal. At the timing t103, the first count value changes to "0" that is the reference value.

At a timing t104, the first data is "H." At the timing t104, "1" that is the second predetermined value is added to the first count value, whereby the first count value changes to "1." Since the first data is "H," at the timing t104, the signal generator 103 generates a valid imaging synchronization signal. At the timing t104, the first count value changes to "0" that is the reference value.

At a timing t105, the first data is "L." At the timing t105, "1" that is the second predetermined value is added to the first count value, whereby the first count value changes to "1." At this time, the first count value is less than "3" that is the first predetermined value. For this reason, at the timing t105, the imaging synchronization signal is invalid.

At a timing t106, the first data is "H." At the timing t106, "1" that is the second predetermined value is added to the first count value, whereby the first count value changes to "2." Since the first data is "H," at the timing t106, the signal generator 103 generates a valid imaging synchronization signal. At the timing t106, the first count value changes to "0" that is the reference value.

At a timing t107 and a timing t108, the first data is "L." At the timing t107 and the timing t108, "1" that is the second predetermined value is added to the first count value. The first count value changes to "1" at the timing t107, and the first count value changes to "2" at the timing t108. At the timing t107 and the timing t108, the first count value is less than "3" that is the first predetermined value. For this reason, at the timing t107 and the timing t108, the imaging synchronization signal is invalid.

At a timing t109, the first data is "L." At the timing t109, "1" that is the second predetermined value is added to the first count value, whereby the first count value changes to "3." At this time, the first count value is "3" or more that is the first predetermined value. For this reason, at the timing t109, the signal generator 103 generates a valid imaging synchronization signal. At the timing t109, the first count value changes to "0" that is the reference value.

At a timing t110, the first data is "H." At the timing t110, "1" that is the second predetermined value is added to the first count value, whereby the first count value changes to "1." Since the first data is "H," at the timing t110, the signal generator 103 generates a valid imaging synchronization signal. At the timing t110, the first count value changes to "0" that is the reference value.

At a timing t111, the first data is "L." At the timing t111, "1" that is the second predetermined value is added to the first count value, whereby the first count value changes to "1." At this time, the first count value is less than "3" that is the first predetermined value. For this reason, at the timing t111, the imaging synchronization signal is invalid.

A detailed description of operations in a period from a timing t112 to a timing t116 will not be presented here. At a timing t113, a timing t114, and a timing t116, the imaging synchronization signal is valid. At a timing t112 and a timing t115, the imaging synchronization signal is invalid.

A second time T2 that is necessary for the first count value to change from the reference value to the first predetermined value is fixed and is longer than the first time T1. The second time T2 is three times the first time T1. The second time T2 may be other than three times the first time T1.

Changes in the first data shown in FIG. 2 are the same as changes in the instruction information shown in FIG. 15. The timing t1002 shown in FIG. 15 corresponds to the timing t102 shown in FIG. 2. The timing t1005 shown in FIG. 15 corresponds to the timing t105 shown in FIG. 2. The timing t1011 shown in FIG. 15 corresponds to the timing a11 shown in FIG. 2. At the timing t1002, the timing t1005, and the timing t1011 shown in FIG. 15, the instruction information is "L," and the imaging synchronization signal is valid. At the timing t102, the timing t105, and the timing a11 shown in FIG. 2, the first data is "L," and the imaging synchronization signal is invalid. For this reason, in the first operation, compared to the operation shown in FIG. 15, unnecessary imaging is reduced.

The timing t1008 shown in FIG. 15 corresponds to the timing t108 shown in FIG. 2. In a period including the timing t1007, the timing t1008, and the timing t1009 shown in FIG. 15 and having a second time T102 as its length, the instruction information is continuously "L." In a period including the timing t107, the timing t108, and the timing t109 shown in FIG. 2 and having a second time T2 as its length, the first data is continuously "L." At the timing t1008 shown in FIG. 15, the imaging synchronization signal is valid. At the timing t108 shown in FIG. 2, the imaging synchronization signal is invalid, and at the timing t109 that is later than the timing t108, the imaging synchronization signal is valid. In the first operation, after a valid imaging synchronization signal is generated in accordance with the first data being "H," in a case in which the first data is continuously "L" for the second time T2 or more, the imaging interval is the second time T2. In other words, in a case in which the movement of the capsule endoscope 10 is small, in the first operation, the imaging interval may be easily configured to be longer than that of the operation shown in FIG. 15. As a result, in the first operation, compared to the operation shown in FIG. 15, unnecessary imaging can easily be decreased.

In the operation shown in FIG. 15, in a case in which the instruction information is "L," regardless whether or not the imaging synchronization signal is valid at the previous timing, an imaging synchronization signal is generated on the basis of only the state of the second synchronization signal. For this reason, after the instruction information becomes "H," in a case in which the instruction information changes to "L," a time interval at which the imaging synchronization signal is generated may be easily configured to be shorter than the second time T102. In other words, the imaging interval may be easily configured to be short.

In the first operation shown in FIG. 2, when a valid imaging synchronization signal is generated, the first count value changes to the reference value. For this reason, after the first data becomes "H," in a case in which the first data changes to "L," compared to the operation shown in FIG. 15, it is difficult for a time interval at which an imaging synchronization signal is generated to be shorter than the second time T2. In other words, it is difficult for the imaging interval to be short.

In a case in which the first data frequently switches between "H" and "L," unnecessary imaging can easily be decreased in accordance with the first operation. For this reason, the power consumption of the capsule endoscope 10 can easily be decreased.

In the first operation, the second predetermined value may be subtracted from the first count value in synchronization with the generation of the first data by the analyzer 101. In such a case, when the first count value becomes the first predetermined value or less, the signal generator 103 generates an imaging synchronization signal.

(Second Operation)

Figure 3:
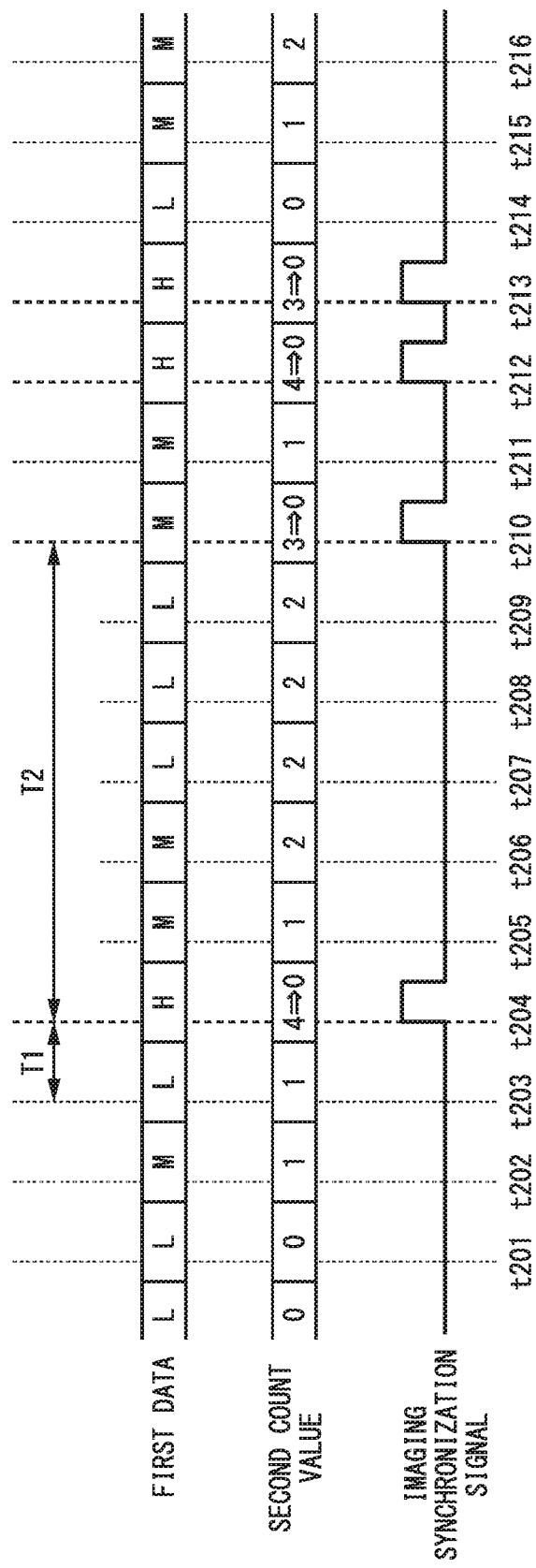
FIG. 3 is a timing diagram showing a second operation of the capsule endoscope according to the first embodiment of the present invention.

FIG. 3 shows a second operation of the capsule endoscope 10. In FIG. 3, waveforms of first data, a second count value, and an imaging synchronization signal are shown. For the imaging synchronization signal, the vertical direction represents the voltage in FIG. 3. In FIG. 3, time advances toward the right side. Points of the second operation shown in FIG. 3 that are different from the first operation shown in FIG. 2 will be described.

The first data is one of "H," "M," and "L." "H" represents that the movement of the capsule endoscope 10 is great. "M" represents that the movement of the capsule endoscope 10 is intermediate. "L" represents that the movement of the capsule endoscope 10 is small. The first data is updated at intervals of the first time T1. There are cases in which updated first data is the same as the first data before update. Compared to the first operation shown in FIG. 2, by increasing the number of states of the first data, an imaging synchronization signal that is more faithful to the movement of the capsule endoscope 10 is generated.

A second count value increases from a reference value. When the second count value becomes a first predetermined value or more, the signal generator 103 generates an imaging synchronization signal. The second count value increases in synchronization with the generation of the first data by the analyzer 101. A value corresponding to the first data is added to the second count value, or a value corresponding to the first data is subtracted from the second count value in synchronization with the generation of the first data by the analyzer 101. The reference value is a third predetermined value different from the first predetermined value.

The counter 102 counts the value corresponding to the first data, thereby generating a second count value. The counter 102 generates the second count value every first time T1. In a case in which the first data is "H," "3" is added to the second count value. In a case in which the first data is "M," "1" is added to the second count value. In a case in which the first data is "L," "0" is added to the second count value. When the second count value becomes the first predetermined value or more, the second count value changes to the reference value. The reference value is "0." The first predetermined value is "3." A second time that is necessary for the second count value to change from the reference value to the first predetermined value is variable.

A cycle at which the signal generator 103 refers to the second count value is fixed. The signal generator 103 refers to the second count value at intervals of the first time T1. The signal generator 103 generates an imaging synchronization signal based on the second count value. In a case in which the second count value is the first predetermined value or more, the signal generator 103 generates an imaging synchronization signal.

At a timing t201, the first data is "L." At the timing t201, "0" is added to the second count value. At this time, the second count value is "0." At this time, the second count value is less than "3" that is the first predetermined value. For this reason, at the timing t201, the imaging synchronization signal is invalid.

At a timing t202, the first data is "M." At the timing t202, "1" is added to the second count value, whereby the second count value changes to "1." At this time, the second count value is less than "3" that is the first predetermined value. For this reason, at the timing t202, the imaging synchronization signal is invalid.

At a timing t203, the first data is "L." At the timing t203, "0" is added to the second count value. At this time, the second count value is "1." At this time, the second count value is less than "3" that is the first predetermined value. For this reason, at the timing t203, the imaging synchronization signal is invalid.

At a timing t204, the first data is "H." At the timing t204, "3" is added to the second count value, whereby the second count value changes to "4." At this time, the second count value is "3" or more that is the first predetermined value. For this reason, at the timing t204, the signal generator 103 generates a valid imaging synchronization signal. At the timing t204, the second count value changes to "0" that is the reference value.

At a timing t205 and a timing t206, the first data is "M." At the timing t205 and the timing t206, "1" is added to the second count value. At the timing t205, the second count value changes to "1," and, at the timing t206, the second count value changes to "2." At the timing t205 and the timing t206, the second count value is less than "3" that is the first predetermined value. For this reason, at the timing t205 and the timing t206, the imaging synchronization signal is invalid.

At a timing t207, a timing t208, and a timing t209, the first data is "L." At the timing t207, the timing t208, and the timing t209, "0" is added to the second count value. At this time, the second count value is "2." At this time, the second count value is less than "3" that is the first predetermined value. For this reason, at the timing t207, the timing t208, and the timing t209, the imaging synchronization signal is invalid.

At a timing t210, the first data is "M." At the timing t210, "1" is added to the second count value, whereby the second count value changes to "3." At this time, the second count value is "3" or more that is the first predetermined value. For this reason, at the timing t210, the signal generator 103 generates a valid imaging synchronization signal. At the timing t210, the second count value changes to "0" that is the reference value.

A detailed description of operations in a period from a timing t211 to a timing t216 will not be presented here. At a timing t212 and a timing t213, the imaging synchronization signal is valid. At the timing t211, a timing t214, a timing t215, and the timing t216, the imaging synchronization signal is invalid.

Since the value added to the second count value is not fixed, a second time T2 that is necessary for the second count value to change from the reference value to the first predetermined value is variable. In FIG. 3, each of a period from the timing t204 to the timing t210, a period from the timing t210 to the timing t212, and a period from the timing t212 to the timing t213 is the second time T2. The maximum value of the second time T2 is longer than the first time T1.

In the second operation shown in FIG. 3, when a valid imaging synchronization signal is generated, the second count value changes to the reference value. For this reason, similar to the first operation shown in FIG. 2, it is difficult for the imaging interval to become short.

In a case in which the first data frequently switches between "H" and "L," unnecessary imaging can easily be decreased in accordance with the second operation. For this reason, the power consumption of the capsule endoscope 10 can be easily decreased.

In the second operation, the value corresponding to the first data may be subtracted from the second count value in synchronization with the generation of the first data by the analyzer 101. In such a case, when the second count value becomes the first predetermined value or less, the signal generator 103 generates an imaging synchronization signal.

(Third Operation)

Figure 4:
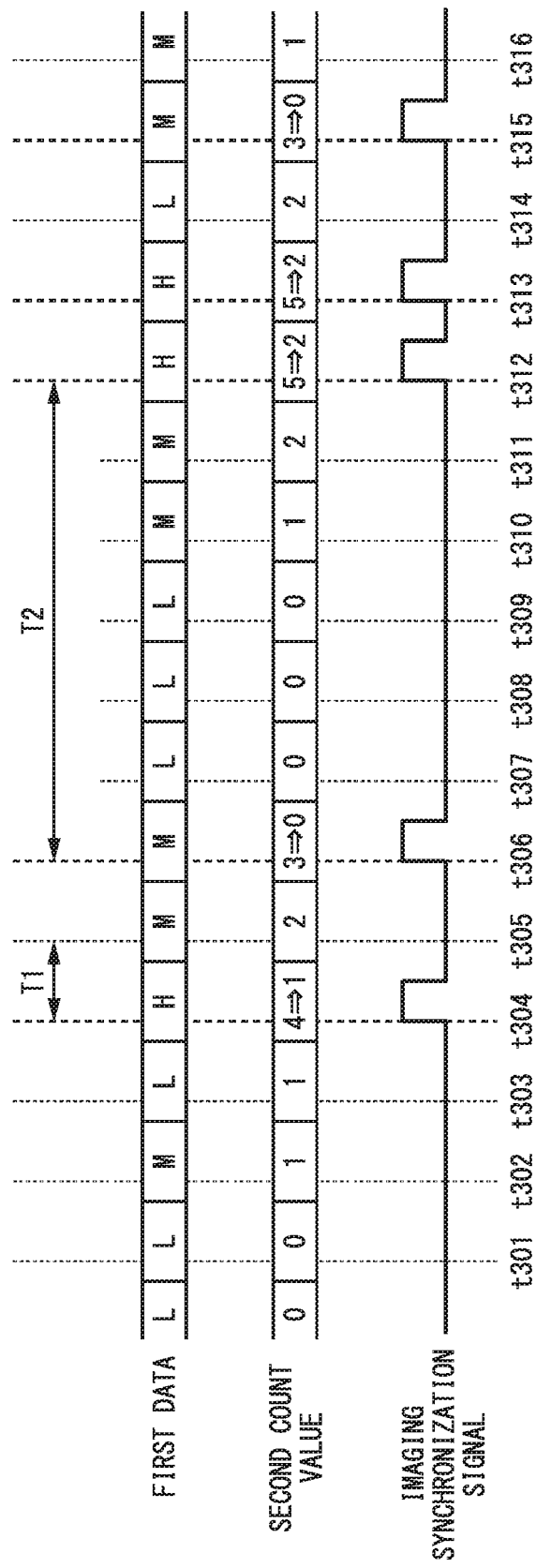
FIG. 4 is a timing diagram showing a third operation of the capsule endoscope according to the first embodiment of the present invention.

FIG. 4 shows a third operation of the capsule endoscope 10. In FIG. 4, waveforms of first data, a second count value, and an imaging synchronization signal are shown. For the imaging synchronization signal, the vertical direction represents the voltage in FIG. 4. In FIG. 4, time advances toward the right side. Points of the third operation shown in FIG. 4 that are different from the second operation shown in FIG. 3 will be described.

When a reference value is less than a first predetermined value and a second count value becomes a first predetermined value or more in accordance with an increase in the second count value from the reference value, the second count value becomes a reference value acquired by subtracting a fourth predetermined value from the second count value. The fourth predetermined value is either the same as the first predetermined value or different from the first predetermined value. The reference value is not always a constant value.

Operations from a timing t301 to a timing t303 are similar to the operations from the timing t201 to the timing t203 in the second operation shown in FIG. 3.

At a timing t304, the first data is "H." At the timing t304, "3" is added to the second count value, whereby the second count value changes to "4." At this time, the second count value is "3" or more that is the first predetermined value. For this reason, at the timing t304, the signal generator 103 generates a valid imaging synchronization signal. At the timing t304, "3" that is the fourth predetermined value is subtracted from the second count value, whereby the second count value changes to "1" that is a reference value.

At a timing t305, the first data is "M." At the timing t305, "1" is added to the second count value, whereby the second count value changes to "2." At this time, the second count value is less than "3" that is the first predetermined value. For this reason, at the timing t305, the imaging synchronization signal is invalid.

At a timing t306, the first data is "M." At the timing t306, "1" is added to the second count value, whereby the second count value changes to "3." At this time, the second count value is "3" or more that is the first predetermined value. For this reason, at the timing t306, the signal generator 103 generates a valid imaging synchronization signal. At the timing t306, "3" that is the fourth predetermined value is subtracted from the second count value, whereby the second count value changes to "0" that is a reference value.

At a timing t307, a timing t308, and a timing t309, the first data is "L." At the timing t307, the timing t308, and the timing t309, "0" is added to the second count value. At this time, the second count value is "0." At this time, the second count value is less than "3" that is the first predetermined value. For this reason, at the timing t307, the timing t308, and the timing t309, the imaging synchronization signal is invalid.

At a timing t310 and a timing t311, the first data is "M." At the timing t310 and the timing t311, "1" is added to the second count value. At the timing t310, the second count value changes to "1," and at the timing t311, the second count value changes to "2." At the timing t310 and the timing t311, the second count value is less than "3" that is the first predetermined value. For this reason, at the timing t310 and the timing t311, the imaging synchronization signal is invalid.

At a timing t312, the first data is "H." At the timing t312, "3" is added to the second count value, whereby the second count value changes to "5." At this time, the second count value is "3" or more that is the first predetermined value. For this reason, at the timing t312, the signal generator 103 generates a valid imaging synchronization signal. At the timing t312, "3" that is the fourth predetermined value is subtracted from the second count value, whereby the second count value changes to "2" that is a reference value.

A detailed description of operations in a period from a timing t313 to a timing t316 will not be presented here. At the timing t313 and a timing t315, the imaging synchronization signal is valid. At a timing t314 and t316, the imaging synchronization signal is invalid.

Since the value added to the second count value is not fixed, a second time T2 that is necessary for the second count value to change from the reference value to the first predetermined value is variable. In FIG. 4, each of a period from the timing t304 to the timing t306, a period from the timing t306 to the timing t312, a period from the timing t312 to the timing t313, and a period from the timing t313 to the timing t315 is the second time T2. The maximum value of the second time T2 is longer than the first time T1.

In the third operation shown in FIG. 4, when a valid imaging synchronization signal is generated, the second count value changes to the reference value. For this reason, similar to the first operation shown in FIG. 2, it is difficult for the imaging interval to become short.

In a case in which the first data frequently switches between "H" and "L," unnecessary imaging can easily be decreased in accordance with the third operation. For this reason, the power consumption of the capsule endoscope 10 can be easily decreased.

When the second count value becomes the first predetermined value or more, the fourth predetermined value is subtracted from the second count value, whereby the second count value changes to a reference value. For this reason, the reference value is based on the second count value before the subtraction of the fourth predetermined value. In other words, a next reference value is set on the basis of the movement of the capsule endoscope 10 when the second count value becomes the first predetermined value or more. As a result, on the basis of the movement of the capsule endoscope 10 when an imaging synchronization signal is generated at a first timing and the movement of the capsule endoscope 10 from the first timing to a second timing, an imaging synchronization signal is generated at the second timing. In other words, the movement of the capsule endoscope 10 for a longer period is reflected in the timing of the imaging synchronization signal.

In the third operation, a value corresponding to the first data may be subtracted from the second count value in synchronization with the generation of the first data by the analyzer 101. In such a case, when the second count value becomes the first predetermined value or less, the signal generator 103 generates an imaging synchronization signal. When the reference value is more than the first predetermined value and the second count value becomes the first predetermined value or less in accordance with a decrease of the second count value from the reference value, the second count value becomes the reference value acquired by adding the fourth predetermined value to the second count value.

(Fourth Operation)

Figure 5:
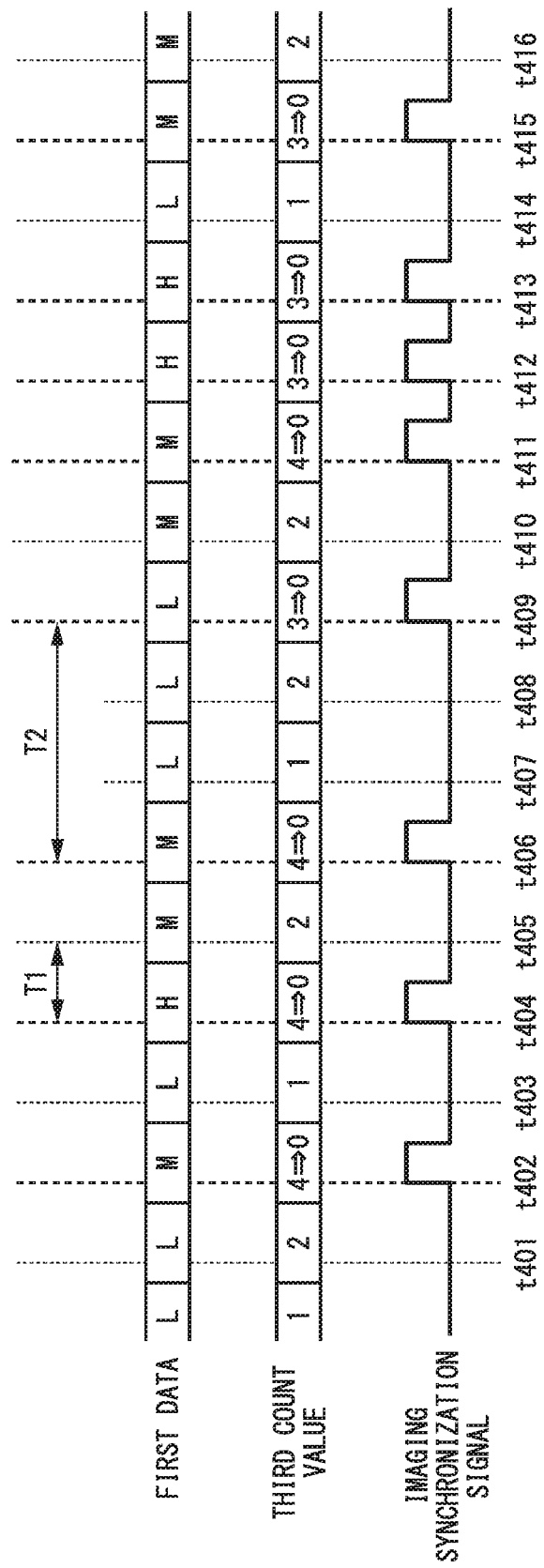
FIG. 5 is a timing diagram showing a fourth operation of the capsule endoscope according to the first embodiment of the present invention.

FIG. 5 shows a fourth operation of the capsule endoscope 10. In FIG. 5, waveforms of first data, a third count value, and an imaging synchronization signal are shown. For the imaging synchronization signal, the vertical direction represents the voltage in FIG. 5. In FIG. 5, time advances toward the right side. Points of the fourth operation shown in FIG. 5 that are different from the first operation shown in FIG. 2 will be described.

A third count value has features of both the first count value in the first operation and the second count value in the second and third operations. The third count value increases from a reference value. When the third count value becomes a first predetermined value or more, the signal generator 103 generates an imaging synchronization signal. The third count value increases in synchronization with the generation of the first data by the analyzer 101. A value acquired by adding the second predetermined value and a value corresponding to the first data is added to the third count value in synchronization with the generation of the first data by the analyzer 101. The second predetermined value is either the same as the first predetermined value or different from the first predetermined value. The reference value is a third predetermined value different from the first predetermined value.

The counter 102 generates a third count value by counting the cycle signal and the value corresponding to the first data. The counter 102 generates a third count value every first time T1. The third count value increases by one every first time T1 on the basis of the cycle signal. In a case in which the first data is "H," "2" is added to the third count value. In a case in which the first data is "M," "1" is added to the third count value. In a case in which the first data is "L," "0" is added to the third count value. When the third count value becomes the first predetermined value or more, the third count value changes to the reference value. The reference value is "0." The first predetermined value is "3." A second time that is necessary for the third count value to change from the reference value to the first predetermined value is variable.

A cycle at which the signal generator 103 refers to the third count value is fixed. The signal generator 103 refers to the third count value at intervals of the first time T1. The signal generator 103 generates an imaging synchronization signal based on the third count value. In a case in which the third count value is the first predetermined value or more, the signal generator 103 generates an imaging synchronization signal.

At a timing t401, the first data is "L." At the timing t401, "1" that is the second predetermined value and "0" based on the first data are added to the third count value. At this time, the third count value is "2." At this time, the third count value is less than "3" that is the first predetermined value. For this reason, at the timing t401, the imaging synchronization signal is invalid.

At a timing t402, the first data is "M." At the timing t402, "1" that is the second predetermined value and "1" based on the first data are added to the third count value, whereby the third count value changes to "4." At this time, the third count value is "3" or more that is the first predetermined value. For this reason, at the timing t402, the signal generator 103 generates a valid imaging synchronization signal. At the timing t402, the third count value changes to "0" that is the reference value.

At a timing t403, the first data is "L." At the timing t403, "1" that is the second predetermined value and "0" based on the first data are added to the third count value, whereby the third count value changes to "1." At this time, the third count value is less than "3" that is the first predetermined value. For this reason, at the timing t403, the imaging synchronization signal is invalid.

At a timing t404, the first data is "H." At the timing t404, "1" that is the second predetermined value and "2" based on the first data are added to the third count value, whereby the third count value changes to "4." At this time, the third count value is "3" or more that is the first predetermined value. For this reason, at the timing t404, the signal generator 103 generates a valid imaging synchronization signal. At the timing t404, the third count value changes to "0" that is the reference value.

At a timing t405, the first data is "M." At the timing t405, "1" that is the second predetermined value and "1" based on the first data are added to the third count value, whereby the third count value changes to "2." At this time, the third count value is less than "3" that is the first predetermined value. For this reason, at the timing t403, the imaging synchronization signal is invalid.

At a timing t406, the first data is "M." At the timing t406, "1" that is the second predetermined value and "1" based on the first data are added to the third count value, whereby the third count value changes to "4." At this time, the third count value is "3," or more that is the first predetermined value. For this reason, at the timing t406, the signal generator 103 generates a valid imaging synchronization signal. At the timing t406, the third count value changes to "0" that is the reference value.

At a timing t407 and a timing t408, the first data is "L." At the timing t407 and the timing t408, "1" that is the second predetermined value and "0" based on the first data are added to the third count value. The third count value changes to "1" at the timing t407, and the third count value changes to "2" at the timing t408. At this time, the third count value is less than "3" that is the first predetermined value. For this reason, at the timing t407 and the timing t408, the imaging synchronization signal is invalid.

At a timing t409, the first data is "L." At the timing t409, "1" that is the second predetermined value and "0" based on the first data are added to the third count value, whereby the third count value changes to "3." At this time, the third count value is "3" or more that is the first predetermined value. For this reason, at the timing t409, the signal generator 103 generates a valid imaging synchronization signal. At the timing t409, the third count value changes to "0" that is the reference value.

A detailed description of operations in a period from a timing t410 to a timing t416 will not be presented here. At a timing t411, a timing t412, a timing t413, and a timing t415, the imaging synchronization signal is valid. At a timing t410, a timing t414, and a timing t416, the imaging synchronization signal is invalid.

Since the value added to the third count value is not fixed, a second time T2 that is necessary for the third count value to change from the reference value to the first predetermined value is variable. In FIG. 5, each of a period from the timing t402 to the timing t404, a period from the timing t404 to the timing t406, a period from the timing t406 to the timing t409, and a period from the timing t409 to the timing t411 is the second time T2. In addition to such times, each of a period from the timing t411 to the timing t412, a period from the timing t412 to the timing t413, and a period from the timing t413 to the timing t415 is the second time T2. The maximum value of the second time T2 is longer than the first time T1.

In the fourth operation shown in FIG. 5, when a valid imaging synchronization signal is generated, the third count value changes to the reference value. For this reason, similar to the first operation shown in FIG. 2, it is difficult for the imaging interval to become short.

In a case in which the first data frequently switches between "H" and "L," unnecessary imaging can easily be decreased in accordance with the fourth operation. For this reason, the power consumption of the capsule endoscope 10 can be easily decreased.

In the fourth operation, a value acquired by adding the second predetermined value and a value corresponding to the first data may be subtracted from the third count value in synchronization with the generation of the first data by the analyzer 101. In such a case, when the third count value becomes the first predetermined value or less, the signal generator 103 generates an imaging synchronization signal.

In the fourth operation, similar to the third operation, when the reference value is less than the first predetermined value, and the third count value becomes the first predetermined value or more in accordance with an increase of the third count value from the reference value, the third count value may become the reference value acquired by subtracting the fourth predetermined value from the third count value. Alternatively, when the reference value is more than the first predetermined value, and the third count value becomes the first predetermined value or less in accordance with a decrease of the third count value from the reference value, the third count value may be the reference value acquired by adding the fourth predetermined value to the third count value.

(Fifth Operation)

Figure 6:
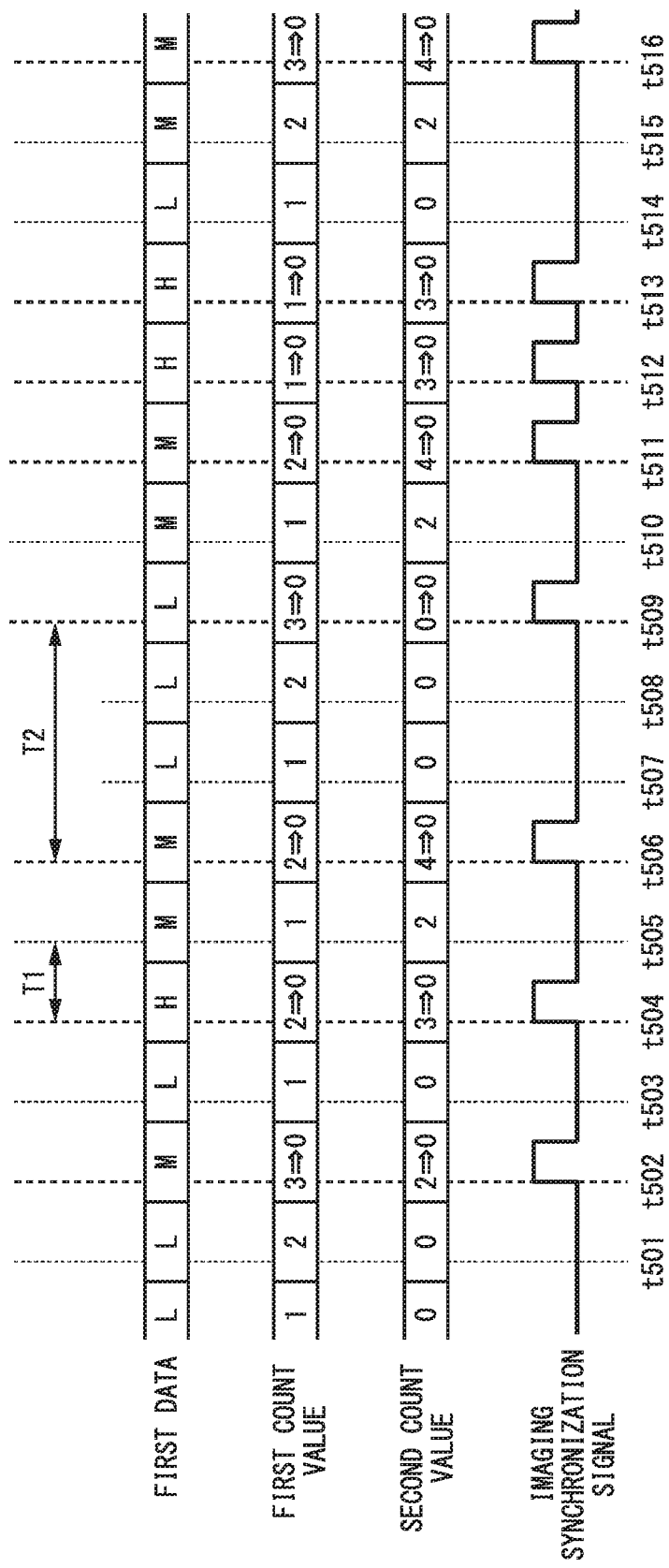
FIG. 6 is a timing diagram showing a fifth operation of the capsule endoscope according to the first embodiment of the present invention.

FIG. 6 shows a fifth operation of the capsule endoscope 10. In FIG. 6, waveforms of first data, a first count value, a second count value, and an imaging synchronization signal are shown. For the imaging synchronization signal, the vertical direction represents the voltage in FIG. 6. In FIG. 6, time advances toward the right side. Points of the operation of the fifth operation shown in FIG. 6 that are different from the first operation shown in FIG. 2 and the second operation shown in FIG. 3 will be described.

The first count value is similar to the first count value described in the first operation. The second count value is similar to the second count value described in the second operation. For example, the counter 102 includes a first counter circuit generating the first count value and a second counter circuit generating the second count value.

The counter 102 generates the first count value by counting the cycle signal and generates the second count value by counting a value corresponding to the first data. The counter 102 generates the first count value and the second count value every first time T1. The first count value increases by a second predetermined value every first time T1 on the basis of the cycle signal. When the first count value becomes a first predetermined value or more, the first count value changes to a reference value. In a case in which the first data is "H," "3" is added to the second count value. In a case in which the first data is "M," "2" is added to the second count value. In a case in which the first data is "L," "0" is added to the second count value. When the second count value becomes the first predetermined value or more, the second count value changes to the reference value. The reference value relating to the first count value and the second count value is "0." The first predetermined value relating to the first count value and the second count value is "3." The second predetermined value relating to the first count value is "1." A second time that is necessary for the first count value to change from the reference value to the first predetermined value is fixed. A second time that is necessary for the second count value to change from the reference value to the first predetermined value is variable. The first predetermined value for the first count value and the first predetermined value for the second count value need not be the same. The reference value for the first count value and the reference value for the second count value need not be the same.

The signal generator 103 generates an imaging synchronization signal on the basis of the first count value and the second count value. A cycle at which the signal generator 103 refers to the first count value and the second count value is fixed. The signal generator 103 refers to the first count value and the second count value at intervals of the first time T1. The signal generator 103 generates an imaging synchronization signal based on the first count value and the second count value. In a case in which at least one of the first count value and the second count value is the first predetermined value or more, the signal generator 103 generates an imaging synchronization signal.

At a timing t501, the first data is "L." At the timing t501, "1" that is the second predetermined value is added to the first count value. At this time, the first count value is "2." At the timing t501, "0" is added to the second count value. At this time, the second count value is "0." At this time, the first count value and the second count value are less than "3" that is the first predetermined value. For this reason, at the timing t501, the imaging synchronization signal is invalid.

At a timing t502, the first data is "M." At the timing t502, "1" that is the second predetermined value is added to the first count value, whereby the first count value changes to "3." At the timing t502, "1" is added to the second count value, whereby the second count value changes to "2." At this time, the first count value is "3" or more that is the first predetermined value. For this reason, at the timing t502, the signal generator 103 generates a valid imaging synchronization signal. At the timing t502, the first count value and the second count value change to "0" that is the reference value.

At a timing t503, the first data is "L." At the timing t503, "1" that is the second predetermined value is added to the first count value, whereby the first count value changes to "1." At the timing t501, "0" is added to the second count value. At this time, the second count value is "0." At this time, the first count value and the second count value are less than "3" that is the first predetermined value. For this reason, at the timing t503, the imaging synchronization signal is invalid.

At a timing t504, the first data is "H." At the timing t504, "1" that is the second predetermined value is added to the first count value, whereby the first count value changes to "2." At the timing t504, "3" is added to the second count value, whereby the second count value changes to "3." At this time, the second count value is "3" or more that is the first predetermined value. For this reason, at the timing t504, the signal generator 103 generates a valid imaging synchronization signal. At the timing t504, the first count value and the second count value change to "0" that is the reference value.

At a timing t505, the first data is "M." At the timing t505, "1" that is the second predetermined value is added to the first count value, whereby the first count value changes to "1." At the timing t505, "2" is added to the second count value, whereby the second count value changes to "2." At this time, the first count value and the second count value are less than "3" that is the first predetermined value. For this reason, at the timing t505, the imaging synchronization signal is invalid.

At a timing t506, the first data is "M." At the timing t506, "1" that is the second predetermined value is added to the first count value, whereby the first count value changes to "2." At the timing t506, "2" is added to the second count value, whereby the second count value changes to "4." At this time, the second count value is "3" or more that is the first predetermined value. For this reason, at the timing t506, the signal generator 103 generates a valid imaging synchronization signal. At the timing t506, the first count value and the second count value change to "0" that is the reference value.

At a timing t507 and a timing t508, the first data is "L." At the timing t507 and the timing t508, "1" that is the second predetermined value is added to the first count value. At the timing t507, the first count value changes to "1," and, at the timing t508, the first count value changes to "2." At the timing t507 and the timing t508, "0" is added to the second count value. At this time, the second count value is "0." At the timing t507 and the timing t508, the first count value and the second count value are less than "3" that is the first predetermined value. For this reason, at the timing t507 and the timing t508, the imaging synchronization signal is invalid.

At a timing t509, the first data is "L." At the timing t509, "1" that is the second predetermined value is added to the first count value, whereby the first count value changes to "3." At the timing t509, "0" is added to the second count value. At this time, the second count value is "0." At this time, the first count value is "3" or more that is the first predetermined value. For this reason, at the timing t509, the signal generator 103 generates a valid imaging synchronization signal. At the timing t509, the first count value and the second count value change to "0" that is the reference value.

A detailed description of operations in a period from a timing t510 to a timing t516 will not be presented here. At a timing t511, a timing t512, a timing t513, and a timing t516, the imaging synchronization signal is valid. At a timing t510, a timing t514, and a timing t515, the imaging synchronization signal is invalid.

A second time T2 that is necessary for the first count value to change from the reference value to the first predetermined value is fixed and is longer than the first time T1. The second time T2 is three times the first time T1. In addition, the second time T2 may be other than three times the first time T1.

Since a value added to the second count value is not fixed, the second time T2 that is necessary for the second count value to change from the reference value to the first predetermined value is variable. In FIG. 6, each of a period from the timing t502 to the timing t504, a period from the timing t504 to the timing t506, a period from the timing t506 to the timing t509, and a period from the timing t509 to the timing t511 is the second time T2. In addition to such times, each of a period from the timing t511 to the timing t512, a period from the timing t512 to the timing t513, and a period from the timing t513 to the timing t516 is the second time T2. The maximum value of the second time T2 is longer than the first time T1.

In the fifth operation shown in FIG. 6, when a valid imaging synchronization signal is generated, the first count value and the second count value change to the reference value. For this reason, similar to the first operation shown in FIG. 2, it is difficult for the imaging interval to become short.

In a case in which the first data frequently switches between "H" and "L," unnecessary imaging can easily be decreased in accordance with the fifth operation. For this reason, the power consumption of the capsule endoscope 10 can be easily decreased.

In the fifth operation, the second predetermined value may be subtracted from the first count value in synchronization with the generation of the first data by the analyzer 101. In such a case, when the first count value becomes the first predetermined value or less, the signal generator 103 generates an imaging synchronization signal.

In the fifth operation, the value corresponding to the first data may be subtracted from the second count value in synchronization with the generation of the first data by the analyzer 101. In such a case, when the second count value becomes the first predetermined value or less, the signal generator 103 generates an imaging synchronization signal.

In the fifth operation, similar to the third operation, when the reference value is less than the first predetermined value, and the first count value or the second count value becomes the first predetermined value or more in accordance with an increase of the first count value or the second count value from the reference value, the first count value or the second count value may be the reference value acquired by subtracting the fourth predetermined value from the first count value or the second count value. Alternatively, when the reference value is more than the first predetermined value, and the first count value or the second count value becomes the first predetermined value or less in accordance with a decrease of the first count value or the second count value from the reference value, the first count value or the second count value may be the reference value acquired by adding the fourth predetermined value to the first count value or the second count value.

As described above, in the first embodiment, when a valid imaging synchronization signal is generated, the count value changes to the reference value. For this reason, the capsule endoscope 10 can control the imaging timing with higher accuracy.

Second Embodiment

Figure 7:
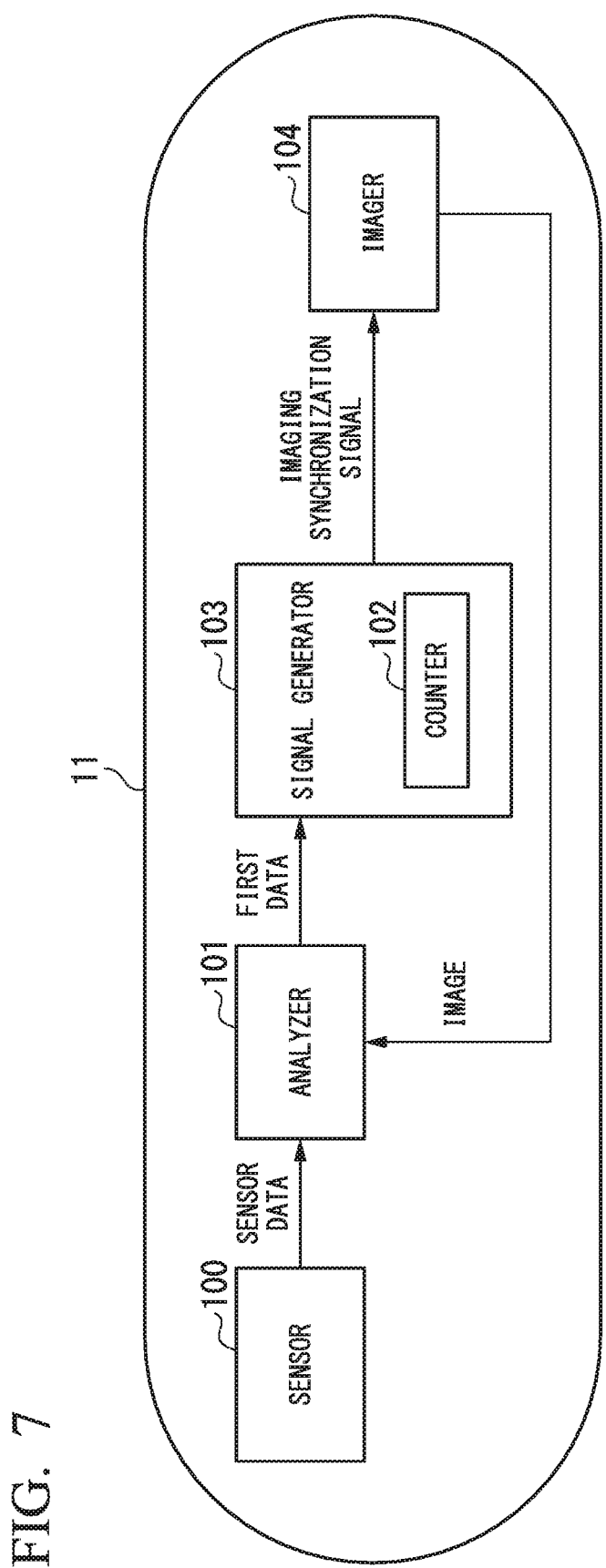
FIG. 7 is a block diagram showing the configuration of a capsule endoscope according to a second embodiment of the present invention.

FIG. 7 shows the configuration of a capsule endoscope 11 according to a second embodiment of the present invention. Points of the configuration shown in FIG. 7 that are different from those of the configuration shown in FIG. 1 will be described.

An analyzer 101 periodically generates first data at intervals of a first time on the basis of second data based on a physical quantity and third data independent from the second data. The analyzer 101 generates second data on the basis of sensor data supplied from a sensor 100. The second data is similar to the first data according to the first embodiment. The third data is data of which a type is different from that of the second data. Alternatively, the third data may be data based on a physical quantity detected from a target object different from a target object of which a physical quantity is detected by the sensor 100. In the example shown in FIG. 7, an image output from an imager 104 is input to the analyzer 101. The analyzer 101 generates third data on the basis of an image.

The analyzer 101 analyzes an image, whereby a relative movement of the capsule endoscope 11 with respect to a human body can be detected. For example, the analyzer 101 calculates a difference between images of two consecutive frames. In a case in which the movement of the capsule endoscope 11 with respect to the human body is great, a difference between the images is a predetermined threshold or more. On the other hand, in a case in which the movement of the capsule endoscope 11 with respect to the human body is small, a difference between the images is less than the predetermined threshold. The analyzer 101 compares the calculated difference with the predetermined threshold. The third data is a result of this comparison.

The other points of the configuration shown in FIG. 7 are similar to those of the configuration shown in FIG. 1.

(Sixth Operation)

Figure 8:
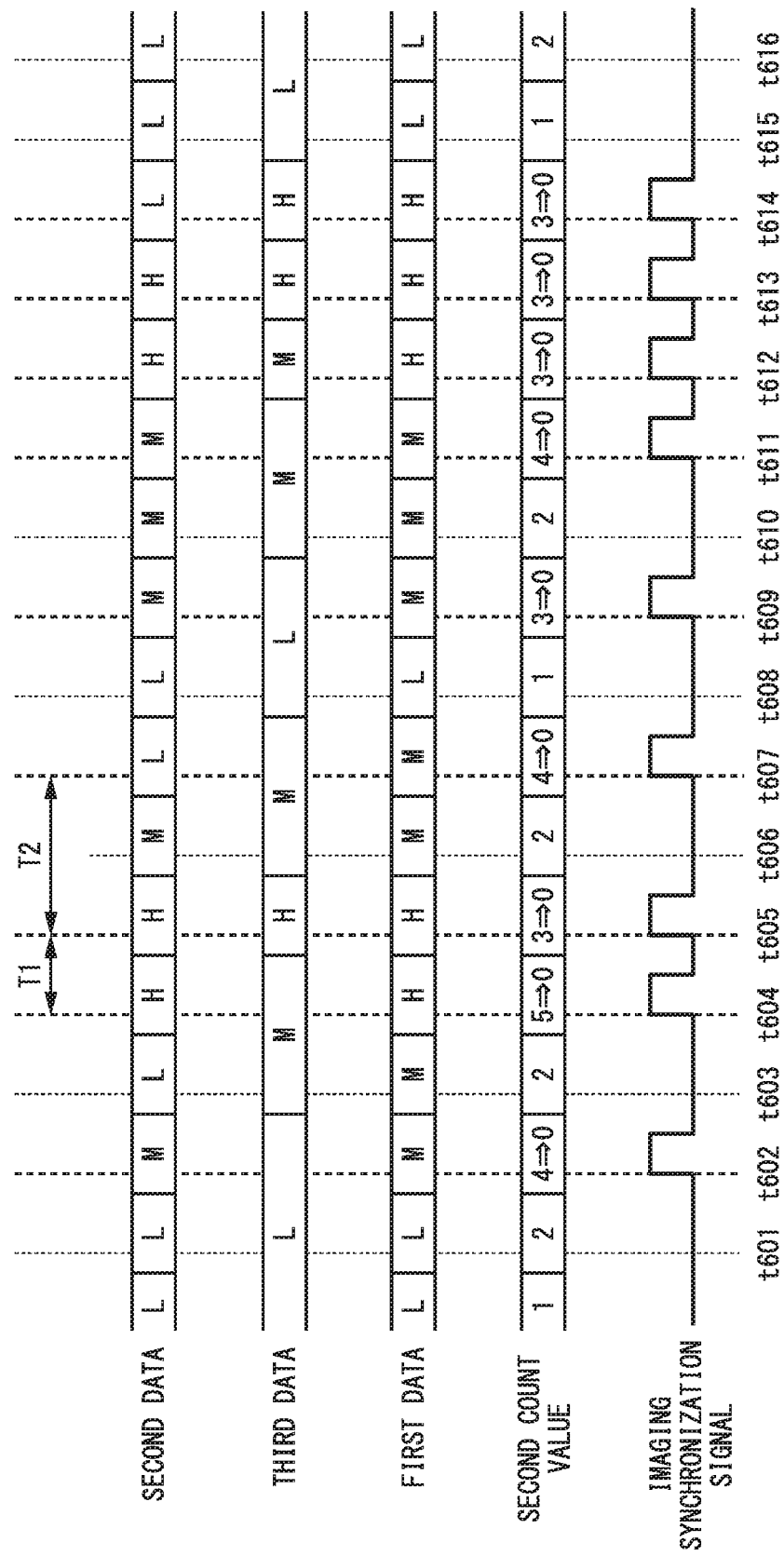
FIG. 8 is a timing diagram showing a sixth operation of the capsule endoscope according to the second embodiment of the present invention.

FIG. 8 shows a sixth operation of the capsule endoscope 11. In FIG. 8, waveforms of second data, third data, first data, a second count value, and an imaging synchronization signal are shown. For the imaging synchronization signal, the vertical direction represents the voltage in FIG. 8. In FIG. 8, time advances toward the right side.

The second data is one of "H," "M," and "L." "H" represents that the movement of the capsule endoscope 11 is great. "M" represents that the movement of the capsule endoscope 11 is medium. "L" represents that the movement of the capsule endoscope 11 is small. The second data is updated at intervals of a first time T1. There are cases in which updated second data is the same as the second data before update.

The third data is one of "H," "M," and "L." The third data is updated after imaging by the imager 104 is performed. There are cases in which updated third data is the same as the third data before update.

The analyzer 101 generates the first data by selecting one of the second data and the third data. More specifically, the analyzer 101 selects one of the second data and the third data that is data representing a greater movement. The analyzer 101 outputs the selected data as first data. The first data is one of "H," "M," and "L."

The counter 102 generates a second count value by counting a value corresponding to the first data. The counter 102 generates the second count value every first time T1. In a case in which the first data is "H," "3" is added to the second count value. In a case in which the first data is "M," "2" is added to the second count value. In a case in which the first data is "L," "1" is added to the second count value. When the second count value becomes a first predetermined value or more, the second count value changes to a reference value. The reference value is "0." The first predetermined value is "3." A second time that is necessary for the second count value to change from the reference value to the first predetermined value is variable.

A cycle at which the signal generator 103 refers to the second count value is fixed. The signal generator 103 refers to the second count value at intervals of the first time T1. The signal generator 103 generates an imaging synchronization signal based on the second count value. In a case in which the second count value is the first predetermined value or more, the signal generator 103 generates an imaging synchronization signal.

At a timing t601, the second data and the third data are "L." For this reason, the first data is "L." At the timing t601, "1" is added to the second count value. At this time, the second count value is "2." At this time, the second count value is less than "3" that is the first predetermined value. For this reason, at the timing t601, the imaging synchronization signal is invalid.

At a timing t602, the second data is "M," and the third data is "L." For this reason, the first data is "M." At the timing t602, "2" is added to the second count value, whereby the second count value changes to "4." At this time, the second count value is "3" or more that is the first predetermined value. For this reason, at the timing t602, the signal generator 103 generates a valid imaging synchronization signal. At the timing t602, the second count value changes to "0" that is the reference value.

At a timing t603, the second data is "L," and the third data is "M." For this reason, the first data is "M." At the timing t603, "2" is added to the second count value, whereby the second count value changes to "2." At this time, the second count value is less than "3" that is the first predetermined value. For this reason, at the timing t603, the imaging synchronization signal is invalid.

At a timing t604, the second data is "H," and the third data is "M." For this reason, the first data is "H." At the timing t604, "3" is added to the second count value, whereby the second count value changes to "5." At this time, the second count value is "3" or more that is the first predetermined value. For this reason, at the timing t604, the signal generator 103 generates a valid imaging synchronization signal. At the timing t604, the second count value changes to "0" that is the reference value.

At a timing t605, the second data and the third data are "H." For this reason, the first data is "H." At the timing t605, "3" is added to the second count value, whereby the second count value changes to "3." At this time, the second count value is "3" or more that is the first predetermined value. For this reason, at the timing t605, the signal generator 103 generates a valid imaging synchronization signal. At the timing t605, the second count value changes to "0" that is the reference value.

At a timing t606, the second data is "M," and the third data is "M." For this reason, the first data is "M." At the timing t606, "2" is added to the second count value, whereby the second count value changes to "2." At this time, the second count value is less than "3" that is the first predetermined value. For this reason, at the timing t606, the imaging synchronization signal is invalid.

At a timing t607, the second data is "L," and the third data is "M." For this reason, the first data is "M." At the timing t607, "2" is added to the second count value, whereby the second count value changes to "4." At this time, the second count value is "3" or more that is the first predetermined value. For this reason, at the timing t607, the signal generator 103 generates a valid imaging synchronization signal. At the timing t607, the second count value changes to "0" that is the reference value.

A detailed description of operations in a period from a timing t608 to a timing t616 will not be presented here. At a timing t609, a timing t611, a timing t612, a timing t613, and a timing t614, the imaging synchronization signal is valid. At the timing t608, a timing t610, a timing t615, and the timing t616, the imaging synchronization signal is invalid.

Since the value added to the second count value is not fixed, a second time T2 that is necessary for the second count value to change from the reference value to the first predetermined value is variable. In FIG. 8, each of a period from the timing t602 to the timing t604, a period from the timing t604 to the timing t605, a period from the timing t605 to the timing t607, and a period from the timing t607 to the timing t609 is the second time T2. In addition to these times, each of a period from the timing t609 to the timing t611, a period from the timing t611 to the timing t612, a period from the timing t612 to the timing t613, and a period from the timing t613 to the timing t614 is the second time T2. The maximum value of the second time T2 is longer than the first time T1.

In the sixth operation shown in FIG. 8, when a valid imaging synchronization signal is generated, the second count value changes to the reference value. For this reason, similar to the first operation shown in FIG. 2, it is difficult for the imaging interval to become short.

In a case in which the first data frequently switches between "H" and "L," unnecessary imaging can easily be decreased in accordance with the sixth operation. For this reason, the power consumption of the capsule endoscope 11 can be easily decreased.

In the sixth operation, the value corresponding to the first data may be subtracted from the second count value in synchronization with the generation of the first data by the analyzer 101. In such a case, when the second count value becomes the first predetermined value or less, the signal generator 103 generates an imaging synchronization signal.

In the sixth operation, similar to the third operation, when a reference value is less than a first predetermined value, and a second count value becomes a first predetermined value or more in accordance with an increase in the second count value from the reference value, the second count value may be a reference value acquired by subtracting a fourth predetermined value from the second count value. Alternatively, when the reference value is more than the first predetermined value, and the second count value becomes the first predetermined value or less in accordance with a decrease of the second count value from the reference value, the second count value may be the reference value acquired by adding the fourth predetermined value to the second count value.

(Seventh Operation)

Figure 9:
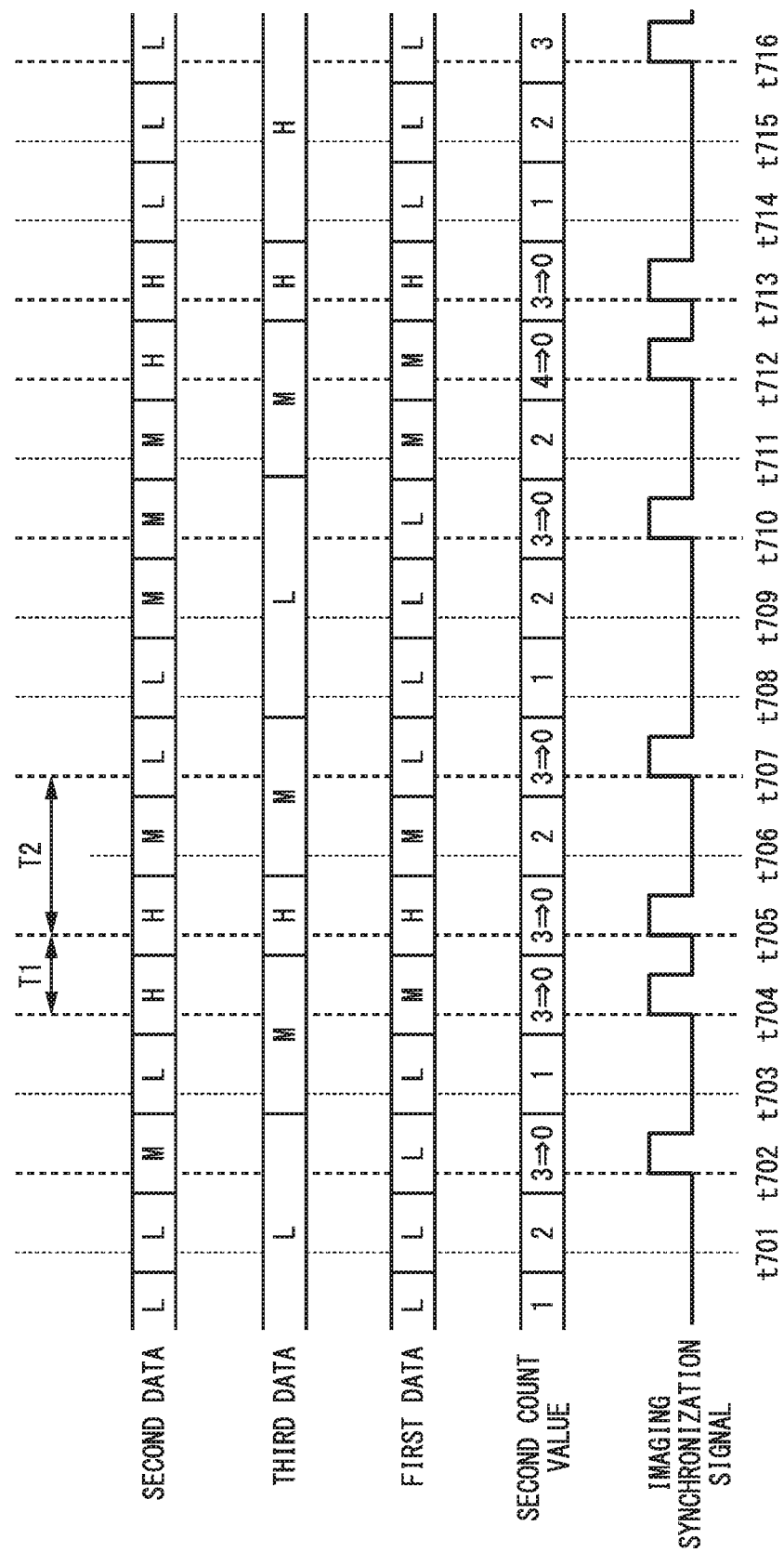
FIG. 9 is a timing diagram showing a seventh operation of the capsule endoscope according to the second embodiment of the present invention.

FIG. 9 shows a seventh operation of the capsule endoscope 11. In FIG. 9, waveforms of second data, third data, first data, a second count value, and an imaging synchronization signal are shown. For the imaging synchronization signal, the vertical direction represents the voltage in FIG. 9. In FIG. 9, time advances toward the right side. Points of the seventh operation shown in FIG. 9 that are different from the sixth operation shown in FIG. 8 will be described.

The analyzer 101 selects one of the second data and the third data that is data representing a smaller movement. The analyzer 101 outputs the selected data as first data.

An operation performed at a timing t701 is similar to the operation performed at the timing t601 shown in FIG. 8. In other words, at the timing t701, the imaging synchronization signal is invalid.

At a timing t702, the second data is "M," and the third data is "L." For this reason, the first data is "L." At the timing t702, "1" is added to the second count value, whereby the second count value changes to "3." At this time, the second count value is "3" or more that is the first predetermined value. For this reason, at the timing t702, the signal generator 103 generates a valid imaging synchronization signal. At the timing t702, the second count value changes to "0" that is the reference value.

At a timing t703, the second data is "L," and the third data is "M." For this reason, the first data is "L." At the timing t703, "1" is added to the second count value, whereby the second count value changes to "1." At this time, the second count value is less than "3" that is the first predetermined value. For this reason, at the timing t703, the imaging synchronization signal is invalid.

At a timing t704, the second data is "H," and the third data is "M." For this reason, the first data is "M." At the timing t704, "2" is added to the second count value, whereby the second count value changes to "3." At this time, the second count value is "3" or more that is the first predetermined value. For this reason, at the timing t704, the signal generator 103 generates a valid imaging synchronization signal. At the timing t704, the second count value changes to "0" that is the reference value.

An operation performed at a timing t705 is similar to the operation performed at the timing t605 shown in FIG. 8. In other words, at the timing t705, the signal generator 103 generates a valid imaging synchronization signal. An operation performed at a timing t706 is similar to the operation performed at the timing t606 shown in FIG. 8. In other words, at the timing t706, the imaging synchronization signal is invalid.

At a timing t707, the second data is "L," and the third data is "M." For this reason, the first data is "L." At the timing t707, "1" is added to the second count value, whereby the second count value changes to "3." At this time, the second count value is "3" or more that is the first predetermined value. For this reason, at the timing t707, the signal generator 103 generates a valid imaging synchronization signal. At the timing t707, the second count value changes to "0" that is the reference value.

A detailed description of operations in a period from a timing t708 to a timing t716 will not be presented here. At a timing t710, a timing t712, a timing t713, and a timing t716, the imaging synchronization signal is valid. At a timing t708, a timing t709, a timing t711, a timing t714, and a timing t715, the imaging synchronization signal is invalid.

In the seventh operation shown in FIG. 9, when a valid imaging synchronization signal is generated, the second count value changes to the reference value. For this reason, similar to the first operation shown in FIG. 2, it is difficult for the imaging interval to become short.

In a case in which the first data frequently switches between "H" and "L," unnecessary imaging can easily be decreased in accordance with the seventh operation. For this reason, the power consumption of the capsule endoscope 11 can be easily decreased.

In the seventh operation, the value corresponding to the first data may be subtracted from the second count value in synchronization with the generation of the first data by the analyzer 101. In such a case, when the second count value becomes the first predetermined value or less, the signal generator 103 generates an imaging synchronization signal.

In the seventh operation, similar to the third operation, when the reference value is less than the first predetermined value, and the second count value becomes the first predetermined value or more in accordance with an increase of the second count value from the reference value, the second count value may become the reference value acquired by subtracting the fourth predetermined value from the second count value. Alternatively, when the reference value is more than the first predetermined value, and the second count value becomes the first predetermined value or less in accordance with a decrease of the second count value from the reference value, the second count value may be the reference value acquired by adding the fourth predetermined value to the second count value.

(Eighth Operation)

Figure 10:
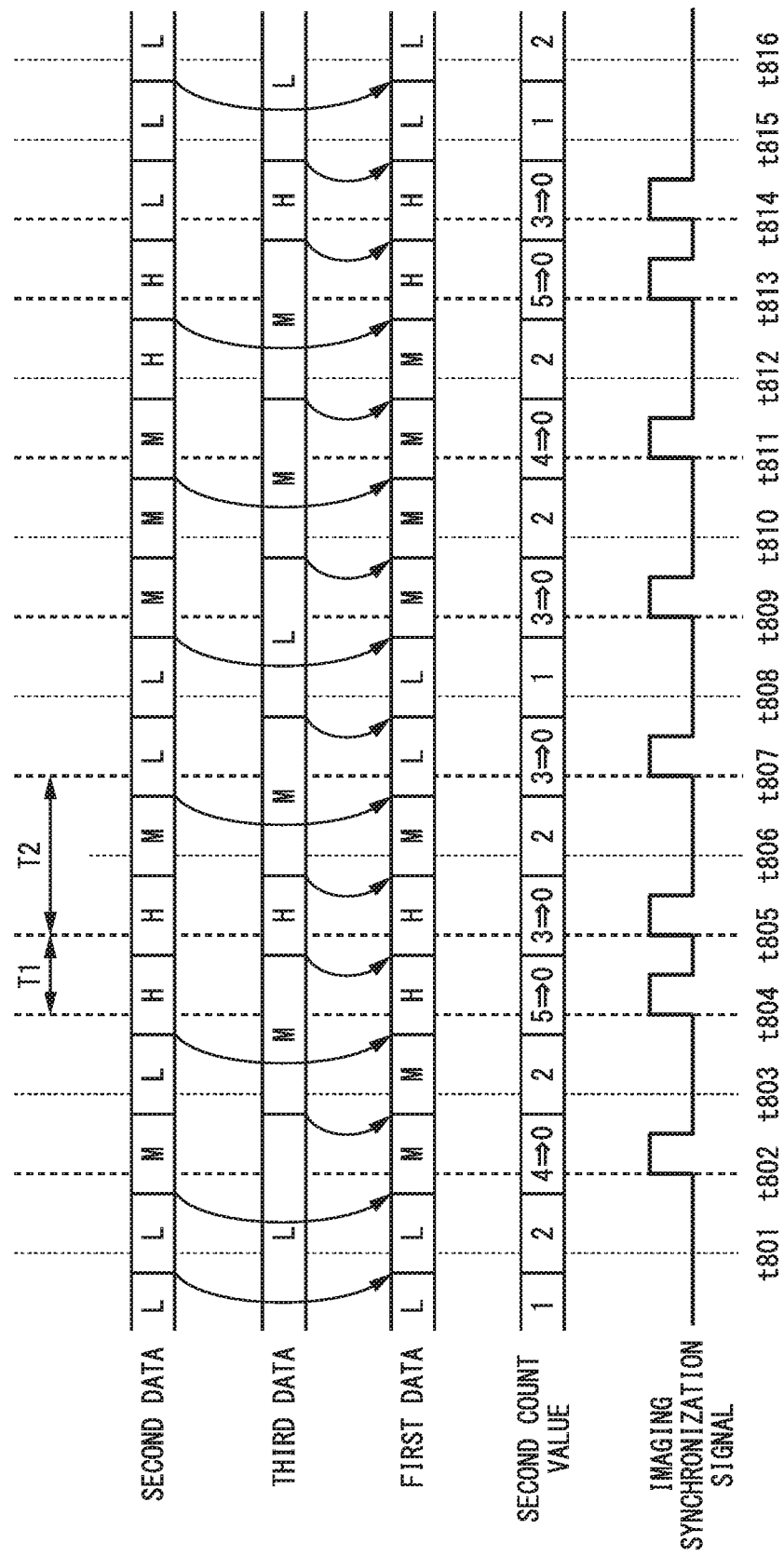
FIG. 10 is a timing diagram showing an eighth operation of the capsule endoscope according to the second embodiment of the present invention.

FIG. 10 shows an eighth operation of the capsule endoscope 11. In FIG. 10, waveforms of second data, third data, first data, a second count value, and an imaging synchronization signal are shown. For the imaging synchronization signal, the vertical direction represents the voltage in FIG. 10. In FIG. 10, time advances toward the right side. Points of the eighth operation shown in FIG. 10 that are different from the sixth operation shown in FIG. 8 will be described.

The analyzer 101 selects the third data only at a timing at which the third data is updated. The analyzer 101 selects the second data at timings other than a timing at which the third data is updated. The analyzer 101 outputs the second data or the third data that has been selected as the first data.

At a timing t801, the second data and the third data are "L." Since the third data has not been updated, the second data is selected. For this reason, the first data is "L." At a timing t801, "1" is added to the second count value. At this time, the second count value is "2." At this time, the second count value is less than "3" that is the first predetermined value. For this reason, at the timing t801, the imaging synchronization signal is invalid.

At a timing t802, the second data is "M," and the third data is "L." Since the third data has not been updated, the second data is selected. For this reason, the first data is "M." At a timing t802, "2" is added to the second count value, whereby the second count value changes to "4." At this time, the second count value is "3" or more that is the first predetermined value. For this reason, at the timing t802, the signal generator 103 generates a valid imaging synchronization signal. At the timing t802, the second count value changes to "0" that is the reference value.

The imager 104 performs imaging on the basis of the imaging synchronization signal generated at the timing t802. Thereafter, the analyzer 101 updates the third data on the basis of an image generated by the imager 104.

At a timing t803, the second data is "L," and the third data is "M." Since the third data has been updated, the third data is selected. For this reason, the first data is "M." At a timing t803, "2" is added to the second count value, whereby the second count value changes to "2." At this time, the second count value is less than "3" that is the first predetermined value. For this reason, at the timing t803, the imaging synchronization signal is invalid.

At a timing t804, the second data is "H," and the third data is "M." Since the third data has not been updated, the second data is selected. For this reason, the first data is "H." At the timing t804, "3" is added to the second count value, whereby the second count value changes to "5." At this time, the second count value is "3" or more that is the first predetermined value. For this reason, at the timing t804, the signal generator 103 generates a valid imaging synchronization signal. At the timing t804, the second count value changes to "0" that is the reference value.

The imager 104 performs imaging on the basis of the imaging synchronization signal generated at the timing t804. Thereafter, the analyzer 101 updates the third data on the basis of the image generated by the imager 104.

At a timing t805, the second data and the third data are "H." Since the third data has been updated, the third data is selected. For this reason, the first data is "H." At the timing t805, "3" is added to the second count value, whereby the second count value changes to "3." At this time, the second count value is "3" or more that is the first predetermined value. For this reason, at the timing t805, the signal generator 103 generates a valid imaging synchronization signal. At the timing t805, the second count value changes to "0" that is the reference value.

The imager 104 performs imaging on the basis of the imaging synchronization signal generated at the timing t805. Thereafter, the analyzer 101 updates the third data on the basis of an image generated by the imager 104.

At a timing t806, the second data is "M," and the third data is "M." Since the third data has been updated, the third data is selected. For this reason, the first data is "M." At a timing t806, "2" is added to the second count value, whereby the second count value changes to "2." At this time, the second count value is less than "3" that is the first predetermined value. For this reason, at the timing t806, the imaging synchronization signal is invalid.

At a timing t807, the second data is "L," and the third data is "M." Since the third data has not been updated, the second data is selected. For this reason, the first data is "L." At a timing t807, "1" is added to the second count value, whereby the second count value changes to "3." At this time, the second count value is "3" or more that is the first predetermined value. For this reason, at the timing t807, the signal generator 103 generates a valid imaging synchronization signal. At the timing t807, the second count value changes to "0" that is the reference value.

A detailed description of operations in a period from a timing t808 to a timing t816 will not be presented here. At timings t809, t811, t813, and t814, the imaging synchronization signal is valid. At timings t808, t810, t812, t815, and t816, the imaging synchronization signal is invalid.

In the eighth operation shown in FIG. 10, when a valid imaging synchronization signal is generated, the second count value changes to the reference value. For this reason, similar to the first operation shown in FIG. 2, it is difficult for the imaging interval to become short.

In a case in which the first data frequently switches between "H" and "L," unnecessary imaging can easily be decreased in accordance with the eighth operation. For this reason, the power consumption of the capsule endoscope 11 can be easily decreased.

In the eighth operation, a value corresponding to the first data may be subtracted from the second count value in synchronization with the generation of the first data by the analyzer 101. In such a case, when the second count value becomes the first predetermined value or less, the signal generator 103 generates an imaging synchronization signal.

In the eighth operation, similar to the third operation, when a reference value is less than a first predetermined value, and a second count value becomes a first predetermined value or more in accordance with an increase in the second count value from the reference value, the second count value may be a reference value acquired by subtracting a fourth predetermined value from the second count value. Alternatively, when the reference value is more than the first predetermined value, and the second count value becomes the first predetermined value or less in accordance with a decrease of the second count value from the reference value, the second count value may be the reference value acquired by adding the fourth predetermined value to the second count value.

In the sixth to the eighth operations, the third count value may be used instead of the second count value. In the sixth to eight operations, similar to the fifth operation shown in FIG. 6, the first count value and the second count value may be used.

As described above, in the second embodiment, when a valid imaging synchronization signal is generated, the count value changes to the reference value. For this reason, the capsule endoscope 11 can control the imaging timing with higher accuracy.

Third Embodiment

Figure 11:
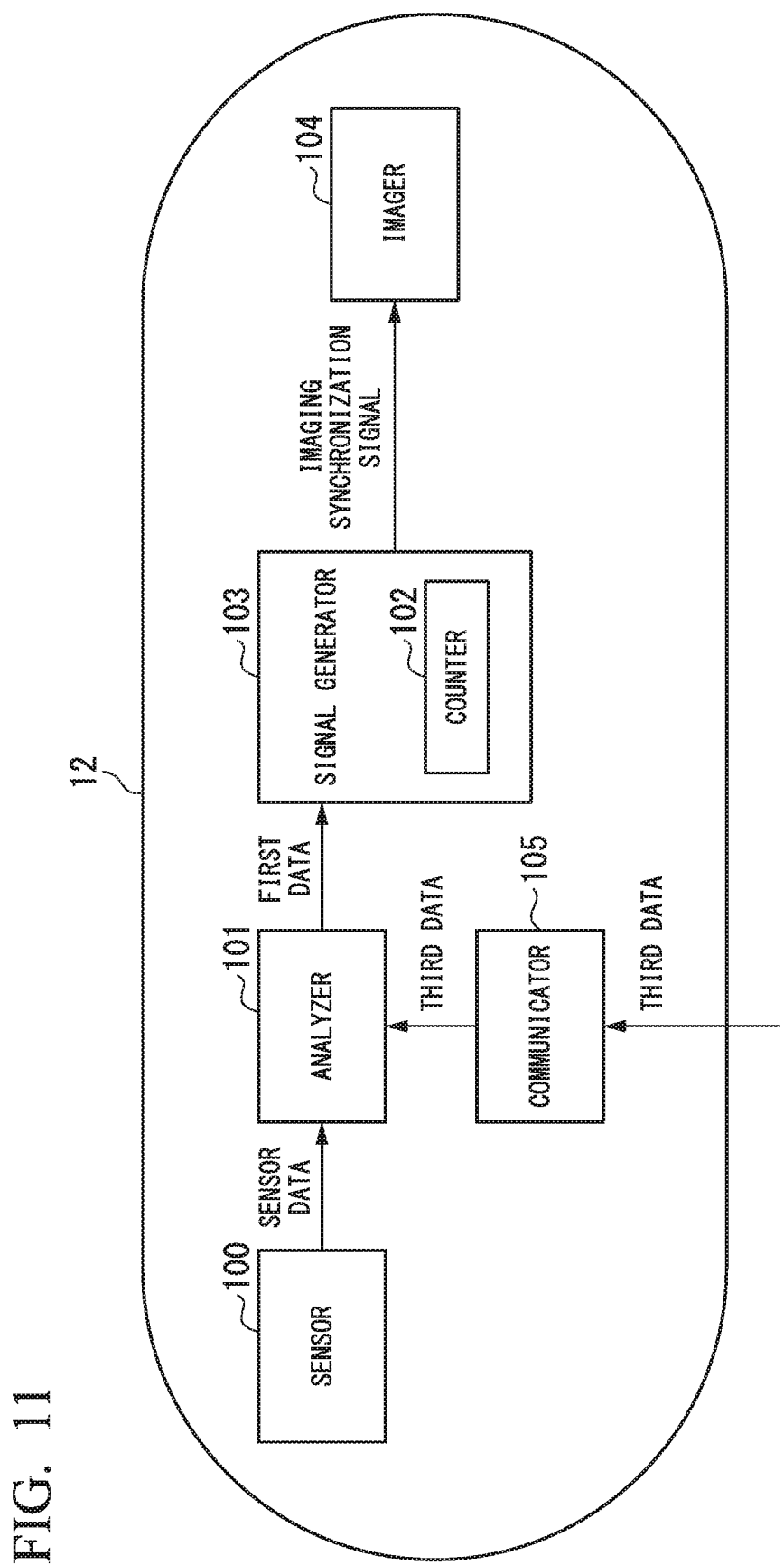
FIG. 11 is a block diagram showing the configuration of a capsule endoscope according to a third embodiment of the present invention.
Figure 12:
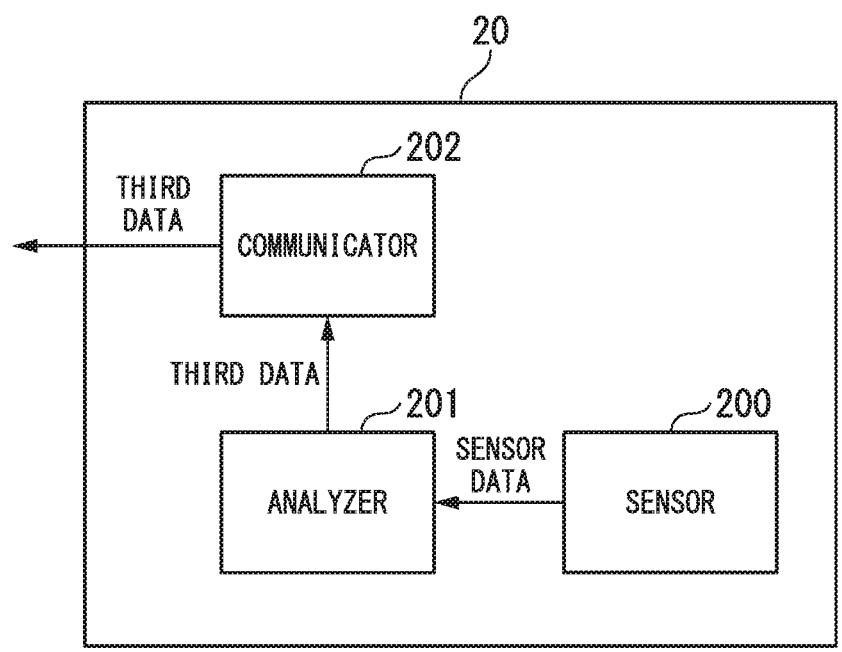
FIG. 12 is a block diagram showing the configuration of a radio communication device according to a third embodiment of the present invention.

A capsule endoscope system according to a third embodiment of the present invention includes the capsule endoscope 12 shown in FIG. 11 and a radio communication device 20 shown in FIG. 12. FIG. 11 shows the configuration of the capsule endoscope 12. Points of the configuration shown in FIG. 11 that are different from those of the configuration shown in FIG. 1 will be described.

The capsule endoscope 12 further includes a communicator 105 in addition to the components included in the capsule endoscope 10 shown in FIG. 1. The communicator 105 is a radio communication circuit (radio communicator). The communicator 105 receives third data from the radio communication device 20. The communicator 105 outputs the third data to an analyzer 101. The communicator 105 may transmit at least one of sensor data generated by a sensor 100 and an image generated by an imager 104 to the radio communication device 20.

Points other than those described above shown in FIG. 11 are similar to those of the configuration shows in FIG. 1.

FIG. 12 shows the configuration of the radio communication device 20. As shown in FIG. 12, the radio communication device 20 includes a sensor 200, an analyzer 201, and a communicator 202. Each component shown in FIG. 12 is hardware.

The sensor 200 generates sensor data. The sensor data generated by the sensor 200 is data of a type different from that of the sensor data generated by the sensor 100. Alternatively, the sensor data generated by the sensor 200 may be data representing a physical quantity detected in a target object different from a target object of which a physical quantity is detected by the sensor 100. For example, the sensor 200 detects the movement of the human body in which the capsule endoscope 12 is disposed and generates sensor data representing the detected movement of the human body. For example, the sensor 200 is at least one of an acceleration sensor, a speed sensor, a magnetic sensor, and an angular velocity sensor. Thus, the sensor 200 can acquire data of at least one of an acceleration, a speed, an angular velocity, and magnetism. The sensor 200 outputs the sensor data to the analyzer 201.

The analyzer 201 is configured as one or a plurality of processors. The analyzer 201 analyzes sensor data and generates third data representing a result of the analysis. The analyzer 201 outputs the third data to the communicator 202.

For example, the analyzer 201 compares sensor data with a predetermined threshold or compares the amount of change of sensor data at a plurality of times with a predetermined threshold. The third data is a result of the comparison described above.

The analyzer 201 may calculate a difference between the sensor data generated by the sensor 100 and the sensor data generated by the sensor 200. In this way, the analyzer 201 can detect a relative movement of the capsule endoscope 12 with respect to the human body. The analyzer 201 may compare the calculated difference with a predetermined threshold. The third data may be a result of this comparison.

The analyzer 201 may detect a relative movement of the capsule endoscope 12 with respect to a human body by analyzing an image acquired by the imager 104. For example, the analyzer 201 calculates a difference between images of consecutive two frames. In a case in which the movement of the capsule endoscope 12 with respect to the human body is great, a difference between the images is a predetermined threshold or more. On the other hand, in a case in which the movement of the capsule endoscope 12 with respect to the human body is small, a difference between the images is less than the predetermined threshold. The analyzer 201 may compare the calculated difference with the predetermined threshold. The third data may be a result of this comparison.

The communicator 202 is a radio communication circuit (radio communicator). The communicator 202 transmits the third data to the capsule endoscope 12. The communicator 202 may receive at least one of the sensor data generated by the sensor 100 and the image generated by the imager 104 from the capsule endoscope 12.

For example, the function of the analyzer 201 can be realized as a function of software by causing a computer of the radio communication device 20 to read and execute a program including commands defining the operation of the analyzer 201. A realization form of this program is similar to the realization form of a program realizing the functions of the analyzer 101 and the signal generator 103.

The operation of the capsule endoscope 12 according to the third embodiment is similar to the operation of the capsule endoscope 11 according to the second embodiment. For this reason, the description of the operation of the capsule endoscope 12 will not be presented here.

In the third embodiment, when a valid imaging synchronization signal is generated, the count value changes to the reference value. For this reason, the capsule endoscope 12 can control the imaging timing with higher accuracy.

Fourth Embodiment

Figure 13:
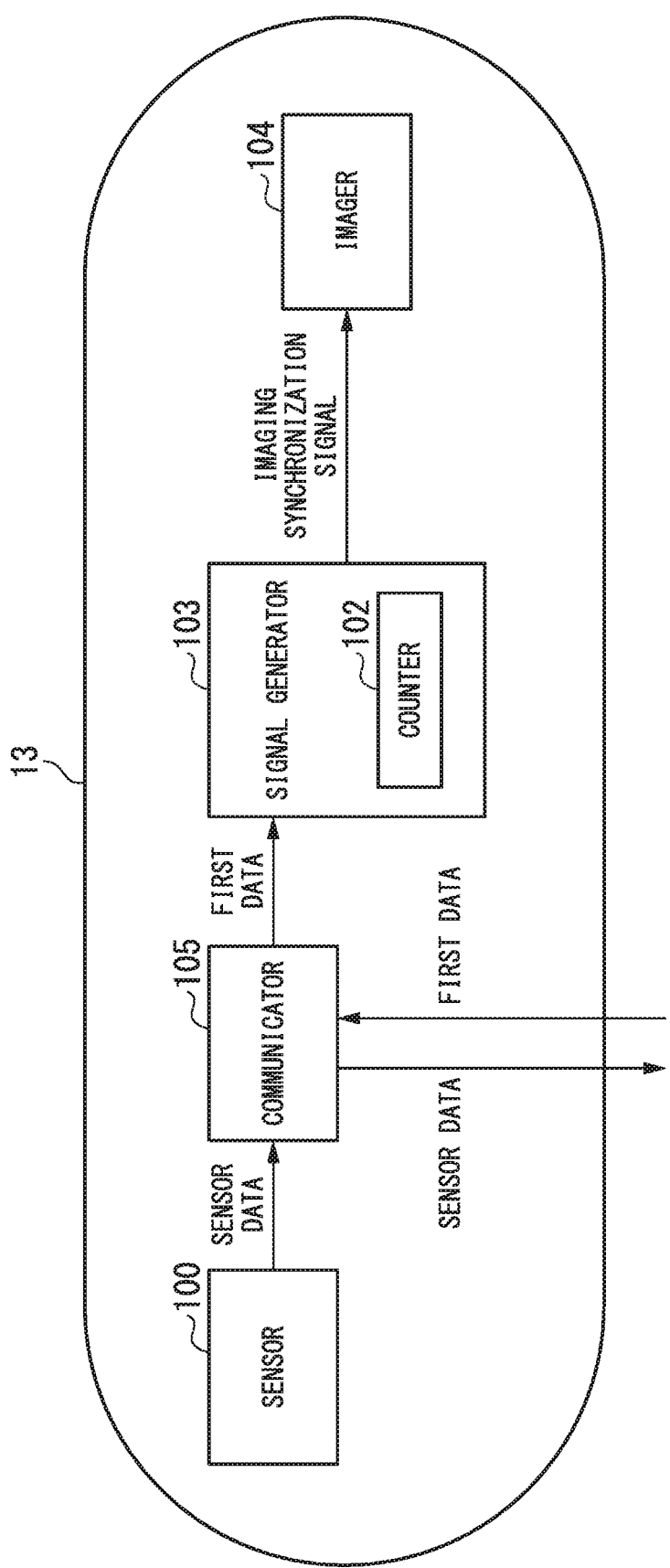
FIG. 13 is a block diagram showing the configuration of a capsule endoscope according to a fourth embodiment of the present invention.
Figure 14:
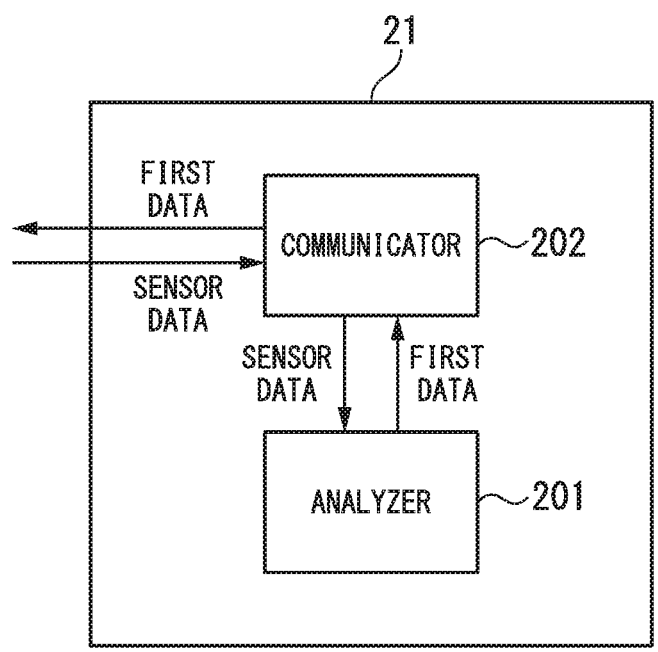
FIG. 14 is a block diagram showing the configuration of a radio communication device according to a fourth embodiment of the present invention.

A capsule endoscope system according to a fourth embodiment of the present invention includes the capsule endoscope 13 shown in FIG. 13 and a radio communication device 21 shown in FIG. 14. FIG. 13 shows the configuration of the capsule endoscope 13. Points of the configuration shows in FIG. 13 that are different from those of the configuration shown in FIG. 11 will be described.

The capsule endoscope 13 does not include the analyzer 101. A sensor 100 outputs sensor data representing a physical quantity detected by the sensor 100 to a communicator 105. The communicator 105 (first communicator) wirelessly transmits the sensor data to the radio communication device 21 and periodically wirelessly receives the first data from the radio communication device 21 at intervals of a first time. The communicator 105 outputs the first data to the signal generator 103.

Points of the configuration shown in FIG. 13 other than the points described above are similar to those of the configuration shown in FIG. 11.

FIG. 14 shows the configuration of the radio communication device 21. As shown in FIG. 14, the radio communication device 21 includes an analyzer 201 and a communicator 202.

The communicator 202 (second communicator) wirelessly receives sensor data from the capsule endoscope 13 and periodically wirelessly transmits the first data to the capsule endoscope 13 at intervals of the first time. The communicator 202 outputs the sensor data to the analyzer 201. The analyzer 201 analyzes a physical quantity detected by the sensor 100 on the basis of the sensor data and periodically generates first data based on the physical quantity at intervals of the first time. The analyzer 201 outputs the first data to the communicator 202.

The capsule endoscope 13 according to the fourth embodiment can perform an operation similar to the operation of the capsule endoscope 10 according to the first embodiment. In other words, in the fourth embodiment, when a valid imaging synchronization signal is generated, the count value changes to the reference value. For this reason, the capsule endoscope 13 can control the imaging timing with higher accuracy.

While preferred embodiments of the invention have been described and shown above, it should be understood that these are exemplars of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A capsule endoscope comprising:
a sensor configured to detect a physical quantity;
one or more processors configured to analyze the physical quantity and periodically generate first data based on the physical quantity at intervals of a first time;
a counter of which a count value increases or decreases from a reference value;
a signal generator configured to generate an imaging synchronization signal on the basis of the first data and generate the imaging synchronization signal on the basis of a result of comparison between the count value and a first predetermined value; and
an image sensor configured to perform imaging on the basis of the imaging synchronization signal,
wherein the count value becomes the reference value when the imaging synchronization signal is generated,
the signal generator is configured to generate the imaging synchronization signal when the count value becomes the first predetermined value or more in accordance with an increase of the count value from the reference value or when the count value becomes the first predetermined value or less in accordance with a decrease of the count value from the reference value,
a second time that is necessary for the count value to change from the reference value to the first predetermined value is fixed or variable,
the second time is longer than the first time in a case in which the second times is fixed, and
the maximum value of the second time is longer than the first time in a case in which the second time is variable.

2. The capsule endoscope according to claim 1,
wherein the reference value include a first reference value and a second reference value, and the second reference value is either the same as the first reference value or different from the first reference value,
the count value becomes the second reference value smaller than the first predetermined value when the first reference value is less than the first predetermined value, and when the count value becomes the first predetermined value or more in accordance with an increase of the count value from the first reference value, and
the count value becomes the second reference value larger than the first predetermined value when the first reference value is more than the first predetermined value and when the count value becomes the first predetermined value or less in accordance with a decrease of the count value from the first reference value.

3. The capsule endoscope according to claim 1, wherein the count value increases in synchronization with generation of the first data by the one or more processors.

4. The capsule endoscope according to claim 3, wherein a second predetermined value is added to the count value in synchronization with the generation of the first data by the one or more processors, and the second predetermined value is either the same as the first predetermined value or different from the first predetermined value.

5. The capsule endoscope according to claim 3, wherein a value corresponding to the first data is added to the count value in synchronization with the generation of the first data by the one or more processors.

6. The capsule endoscope according to claim 3, wherein a value acquired by adding a second predetermined value and a value corresponding to the first data is added to the count value in synchronization with the generation of the first data by the one or more processors, and the second predetermined value is either the same as the first predetermined value or different from the first predetermined value.

7. The capsule endoscope according to claim 1, wherein the count value decreases in synchronization with generation of the first data by the one or more processors.

8. The capsule endoscope according to claim 7, wherein a second predetermined value is subtracted from the count value in synchronization with the generation of the first data by the one or more processors, and the second predetermined value is either the same as the first predetermined value or different from the first predetermined value.

9. The capsule endoscope according to claim 7, wherein a value corresponding to the first data is subtracted from the count value in synchronization with the generation of the first data by the one or more processors.

10. The capsule endoscope according to claim 7, wherein a value acquired by adding the second predetermined value and the value corresponding to the first data is subtracted from the count value in synchronization with the generation of the first data by the one or more processors, and the second predetermined value is either the same as the first predetermined value or different from the first predetermined value.

11. The capsule endoscope according to claim 1, wherein the reference value is a third predetermined value different from the first predetermined value.

12. The capsule endoscope according to claim 1,
wherein the count value becomes the reference value by subtracting a fourth predetermined value from the count value when the reference value is less than the first predetermined value and when the count value becomes the first predetermined value or more in accordance with an increase of the count value from the reference value,
the count value becomes the reference value acquired by adding the fourth predetermined value to the count value when the reference value is more than the first predetermined value and when the count value becomes the first predetermined value or less in accordance with a decrease of the count value from the reference value, and
the fourth predetermined value is either the same as the first predetermined value or different from the first predetermined value.

13. The capsule endoscope according to claim 1, wherein the one or more processors is configured to periodically generate the first data at intervals of the first time on the basis of second data based on the physical quantity and on the basis of third data that is independent from the second data.

14. The capsule endoscope according to claim 1,
wherein the sensor is configured to periodically detect a movement of the capsule endoscope at intervals of a third time, the third time being the first time or less, and
the one or more processors is configured to analyze the movement and periodically generate the first data based on the movement at intervals of the first time.

15. A capsule endoscope system comprising:
a capsule endoscope; and
a radio communication device,
wherein the capsule endoscope includes:
　a sensor configured to detect a physical quantity;
　a first transceiver configured to wirelessly transmit sensor data representing the physical quantity to the radio communication device and wirelessly receive first data from the radio communication device periodically at intervals of a first time;
　a counter of which a count value increases or decreases from a reference value;
　a signal generator configured to generate an imaging synchronization signal on the basis of the first data and generate the imaging synchronization signal on the basis of a result of comparison between the count value and a first predetermined value; and
　an image sensor configured to perform imaging on the basis of the imaging synchronization signal,
wherein the radio communication device includes:
　a second transceiver configured to wirelessly receive the sensor data from the capsule endoscope and wirelessly transmit the first data to the capsule endoscope periodically at intervals of the first time; and
　one or more processors configured to analyze the physical quantity on the basis of the sensor data and periodically generate the first data based on the physical quantity at intervals of the first time,
the count value becomes the reference value when the imaging synchronization signal is generated,
the signal generator is configured to generate the imaging synchronization signal when the count value becomes the first predetermined value or more in accordance with an increase of the count value from the reference value or when the count value becomes the first predetermined value or less in accordance with a decrease of the count value from the reference value,
a second time that is necessary for the count value to change from the reference value to the first predetermined value is fixed or variable, the second time is longer than the first time in a case in which the second times is fixed, and the maximum value of the second time is longer than the first time in a case in which the second time is variable.

* * * * *